United States Patent
Phillips et al.

(10) Patent No.: US 6,241,674 B1
(45) Date of Patent: Jun. 5, 2001

(54) MEDICAL ULTRASOUND DIAGNOSTIC IMAGING METHOD AND SYSTEM WITH NONLINEAR PHASE MODULATION PULSE COMPRESSION

(75) Inventors: Patrick Phillips, Sunnyvale; Gregory L. Holley, Mountain View; David J. Napolitano, Pleasanton; Kutay F. Ustuner, Mountain View, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/282,510

(22) Filed: Mar. 31, 1999

(51) Int. Cl.⁷ ................................................ A61B 8/00
(52) U.S. Cl. ............................................................. 600/443
(58) Field of Search ........................... 600/437, 440–441, 600/443, 447, 454–456, 458; 367/7, 11, 103–105; 73/675–676

(56) References Cited

U.S. PATENT DOCUMENTS

| | | |
|---|---|---|
| 4,403,311 | 9/1983 | Tournois . |
| 4,403,314 | 9/1983 | Tournois . |
| 4,456,982 | 6/1984 | Tournois . |
| 4,458,342 | 7/1984 | Tournois . |
| 5,014,712 | 5/1991 | O'Donnell . |
| 5,142,649 | 8/1992 | O'Donnell . |
| 5,224,482 | 7/1993 | Nikoonahad et al. . |
| 5,454,372 | 10/1995 | Banjanin et al. . |
| 5,522,393 | 6/1996 | Phillips . |
| 5,608,690 | 3/1997 | Hossack et al. . |
| 5,675,554 | 10/1997 | Cole et al. . |
| 5,851,187 | 12/1998 | Thomas, III et al. . |
| 5,961,463 | * 10/1999 | Rhyne et al. ........................ 600/458 |
| 5,964,706 | * 10/1999 | Mo et al. .............................. 600/443 |
| 5,980,459 | * 11/1999 | Chiao et al. ......................... 600/447 |
| 6,010,456 | 1/2000 | Rhyne . |
| 6,050,947 | 4/2000 | Rhyne et al. . |
| 6,095,977 | * 8/2000 | Hall et al. ............................ 600/443 |

OTHER PUBLICATIONS

Takeuchi, Y., Coded Excitation for Harmonics Imaging, 1996 IEE Ultrasonics Symposium, pp. 1433–1436.

"Complementary Series," Marcel J.E. Golay, *IRE Transactions on Information Theory*, vol. IT 7, Jan. 1961, No. 1, pp. 82–87.

"Golay's Complementary Series", *IRE Transactions on Information Theory*, vol. IT–7, Oct., 1961, No. 4, pp. 273–276.

"Properties of Swept FM Waveforms in Medical Ultrasound Imaging," C.R. Cole, Acuson Corporation, Mountain View, California.

(List continued on next page.)

Primary Examiner—Francis J. Jaworski
(74) Attorney, Agent, or Firm—Brinks Hofer Gilson & Lione

(57) ABSTRACT

A medical ultrasonic diagnostic imaging method and apparatus uses a phased array transducer probe to transmit a fundamental coded ultrasonic pulse into a tissue. This pulse has a time-bandwidth product that is greater than 1 but less than 100. A receiver is coupled to the probe to receive an Nth harmonic echo signal from the tissue, and a compression filter compresses the harmonic echo signal with a compression function having a phase that varies about N times as fast as the fundamental coded ultrasonic pulse. In this way, the SNR of the resulting image is increased. The disclosed method and apparatus are particularly well adapted for use with tissue harmonic imaging, because of the typically low SNR characteristic of such imaging. Other aspects are well-suited for imaging with non-linear contrast agents.

72 Claims, 17 Drawing Sheets

OTHER PUBLICATIONS

"Acoustical Imaging Via Coherent Reception of Spatially Coloured Transmissions," P. Tournois, *1980 IEEE, 1980 Ultrasonics Symposium*, pp. 747–750.

"Multibeam Imaging Using Spatially Variant Insonification," Jules S. Jaffe and Phillipe M. Cassereau, *J. Acoust. Soc. Am.* 83 (4), Apr. 1988, pp. 1458–1464.

"Coded Excitation System for Improving the Penetration of Real–Time Phased–Array Imaging Systems," Matthew O'Donnell, *IEEE Transactions on Ultrasonics, Ferroelectrics, and Frequency Control*, vol. 39, No. 3, May 1992, pp. 341–351.

"Filter–Based Coded–Excitation System for High–Speed Ultrasonic Imaging," Jian Shen and Emad S. Ebbini, *IEEE Transactions on Medical Imaging*, vol. 17, No. 6, Dec. 1998, pp. 923–934.

"Coded Excitation for Harmonic Imaging," Y. Takeuchi, Ultrasonics, PH–3, 1996.

"Chirped Excitation for <–100dB Time Sidelobe Echo Sounding," Y. Takeuchi.

"Simultaneous MultiFrequency Ultrasonography The Principle and Technology," Miwa et al., 1981 Ultrasonics Symposium, pp. 655–659.

"Echography Using Correlation Techniques: Choice of Coding Signal," Benkhelifa et al., 1994 IEEE, pp. 579–587.

"Real–Time Two–Dimensional Doppler Flow Mapping Using Auto–Correlation," C. Kasai et al., pp. 447–460.

"Radar Signals, an Introduction to Theory and Application," C. Cook et al., Chapter 3.

\* cited by examiner

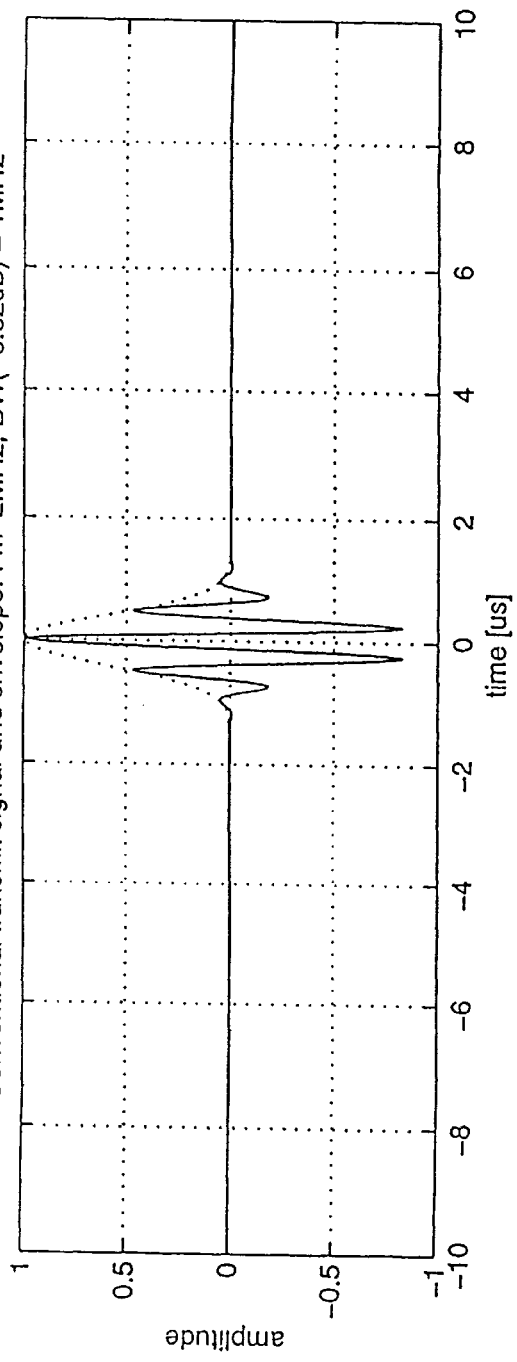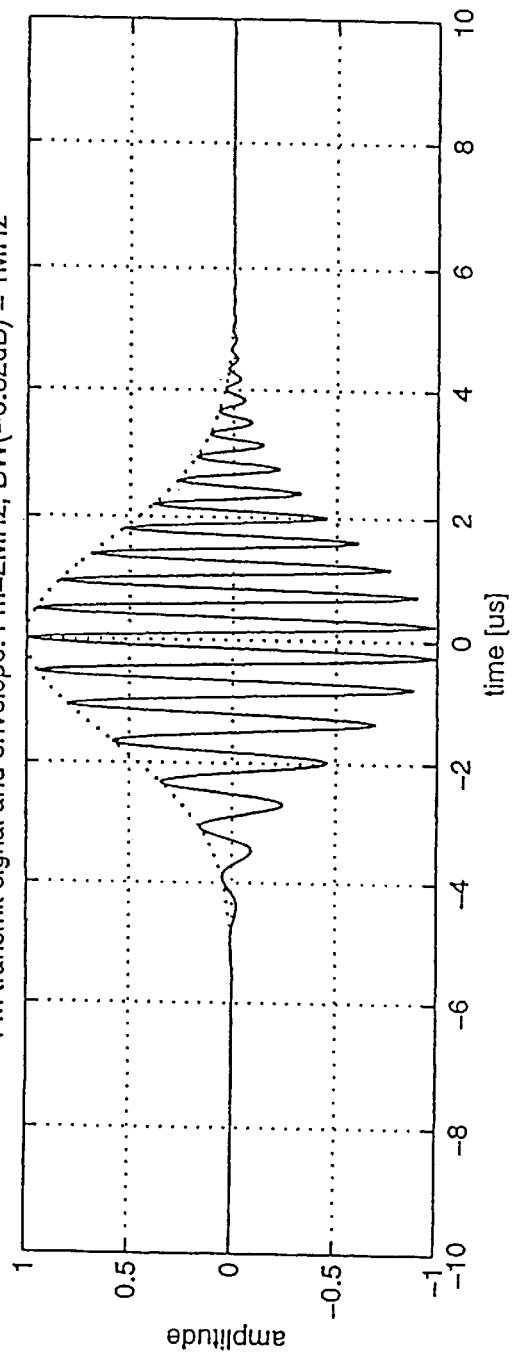

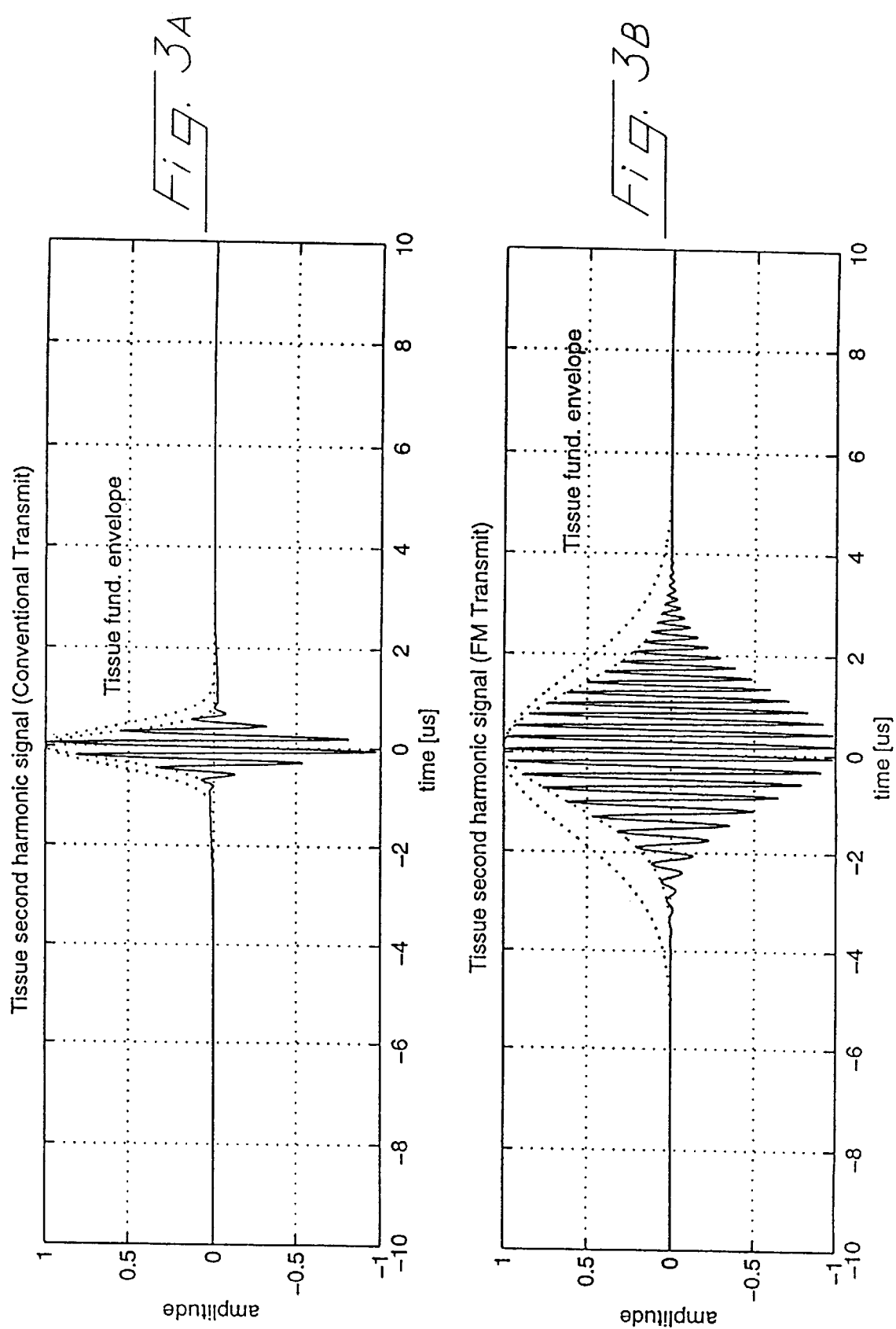

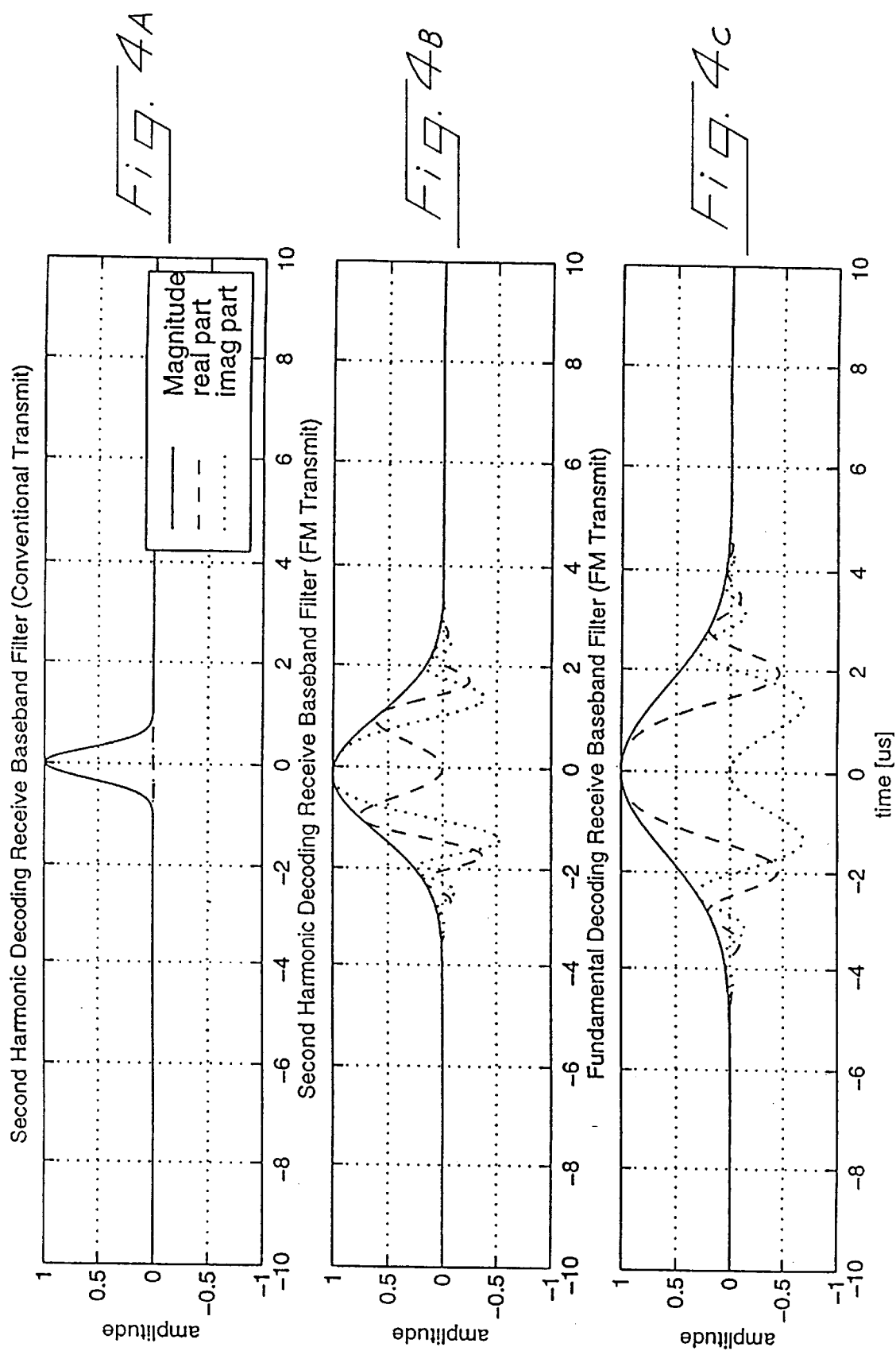

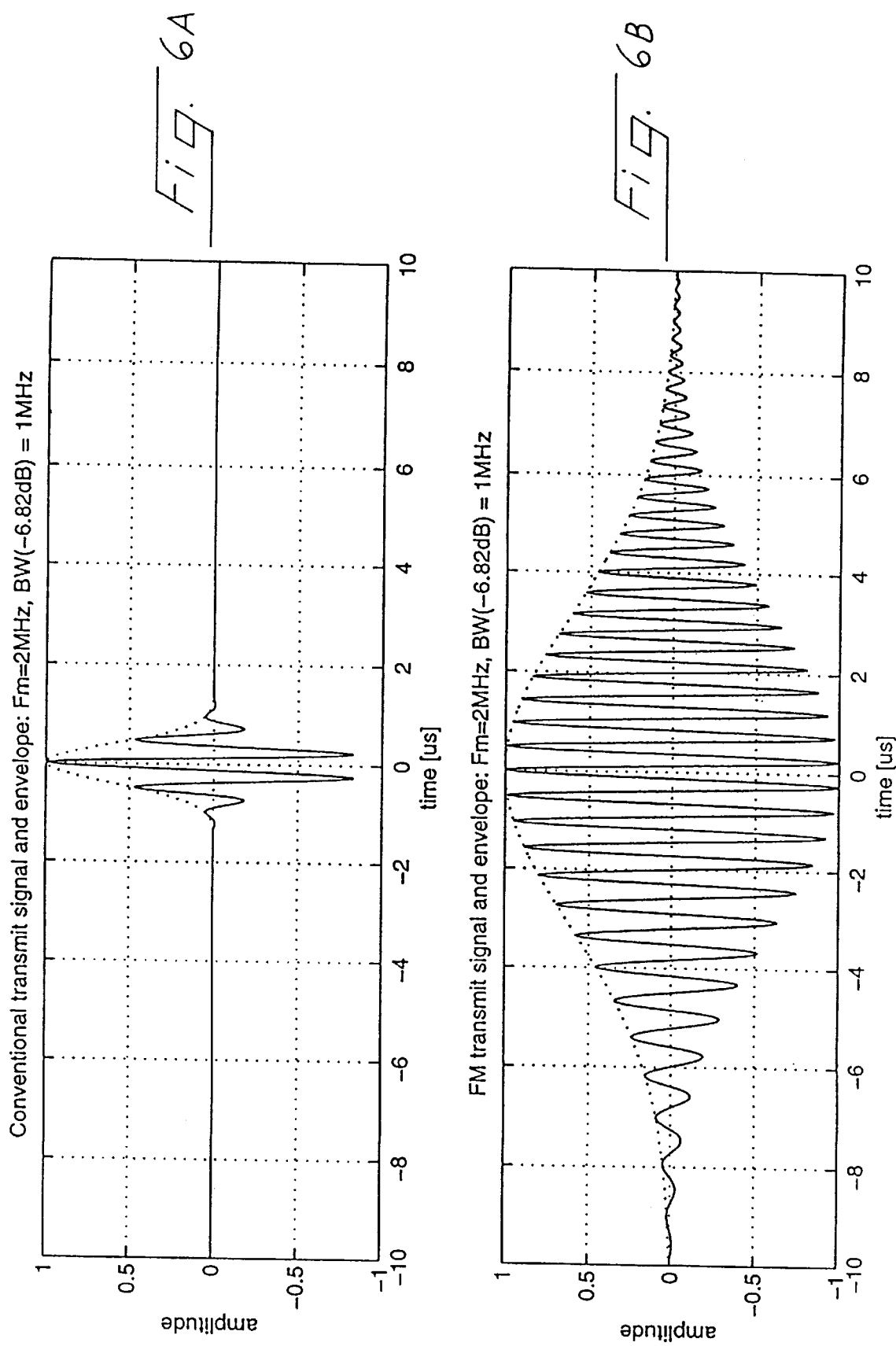

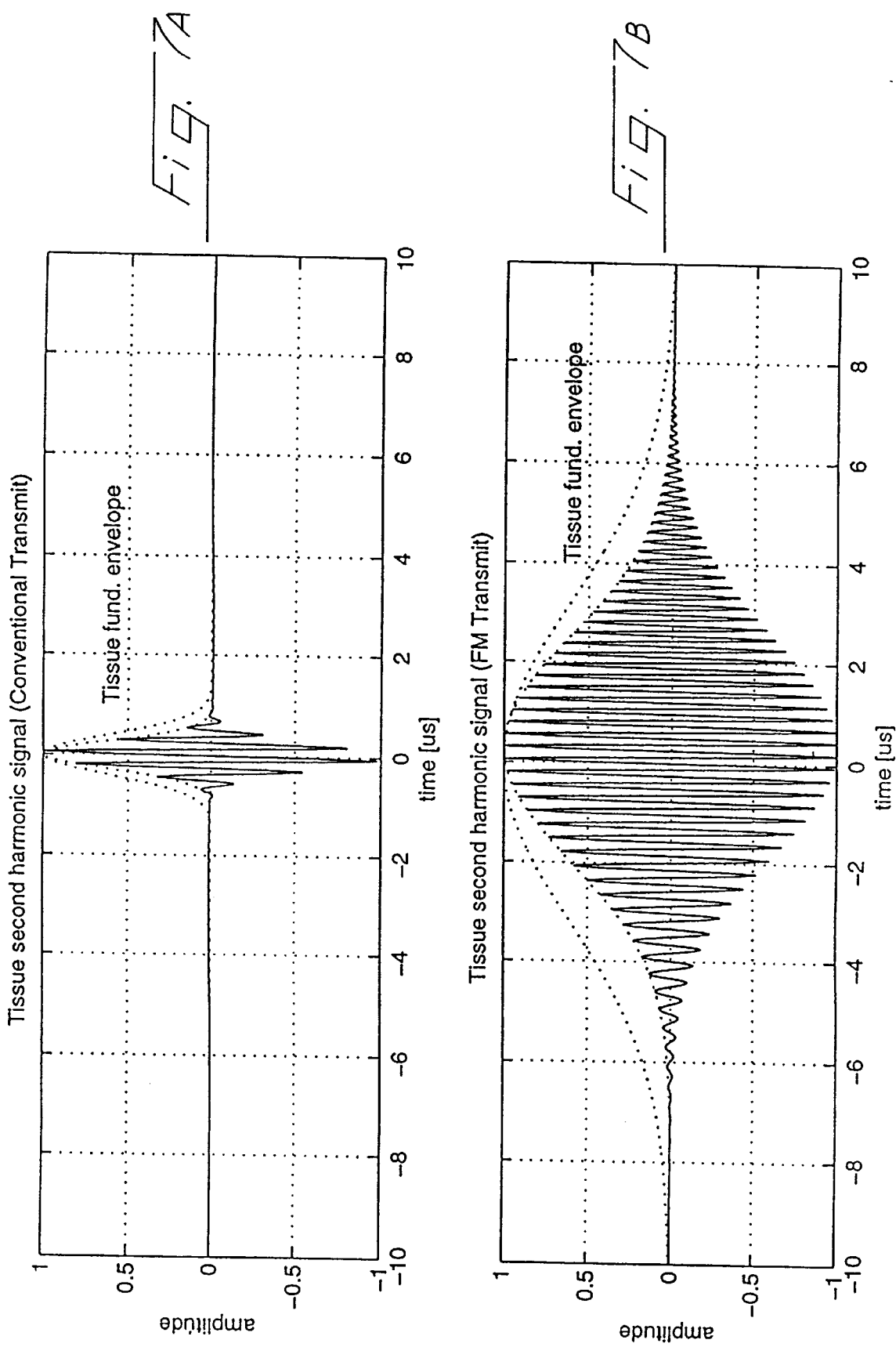

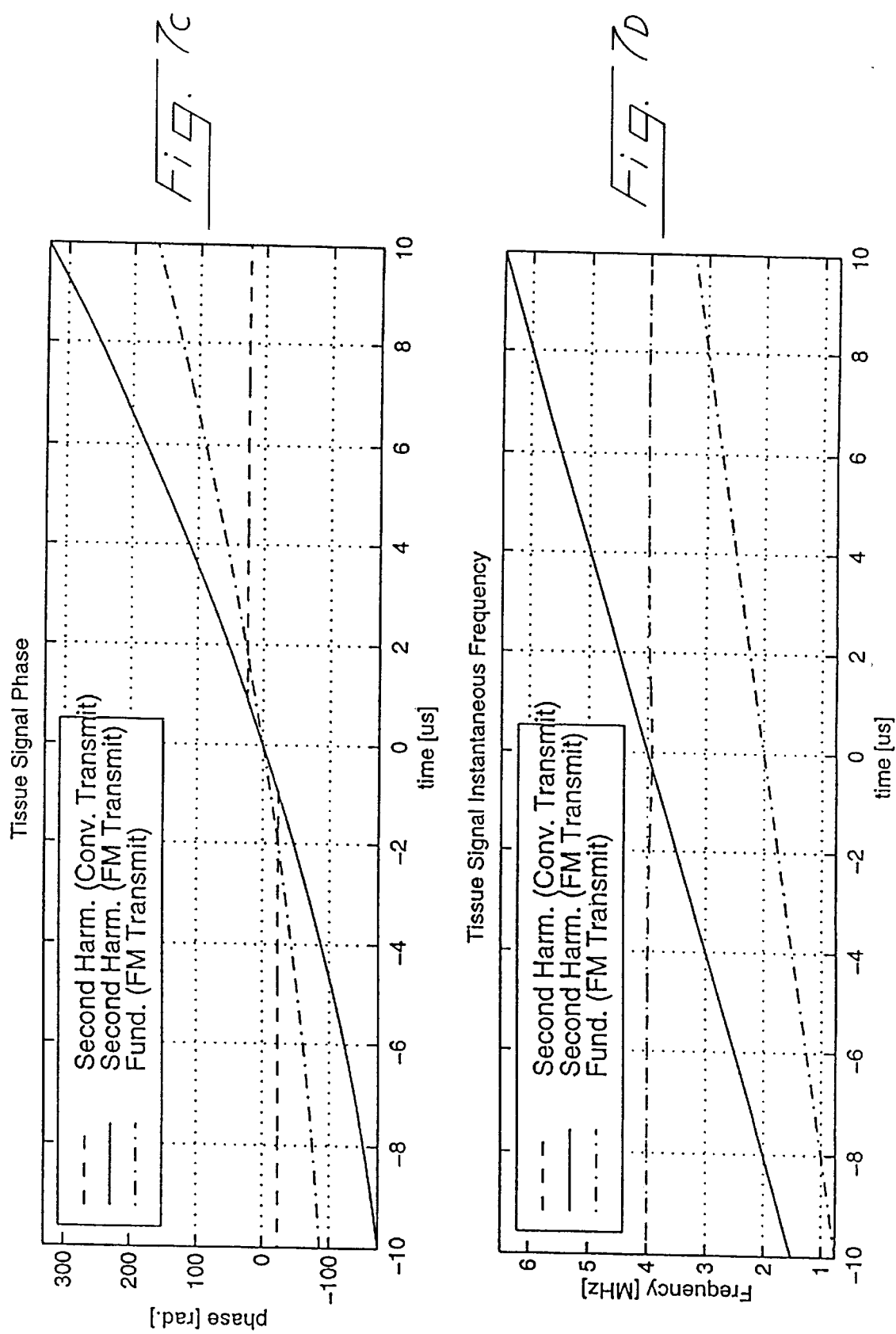

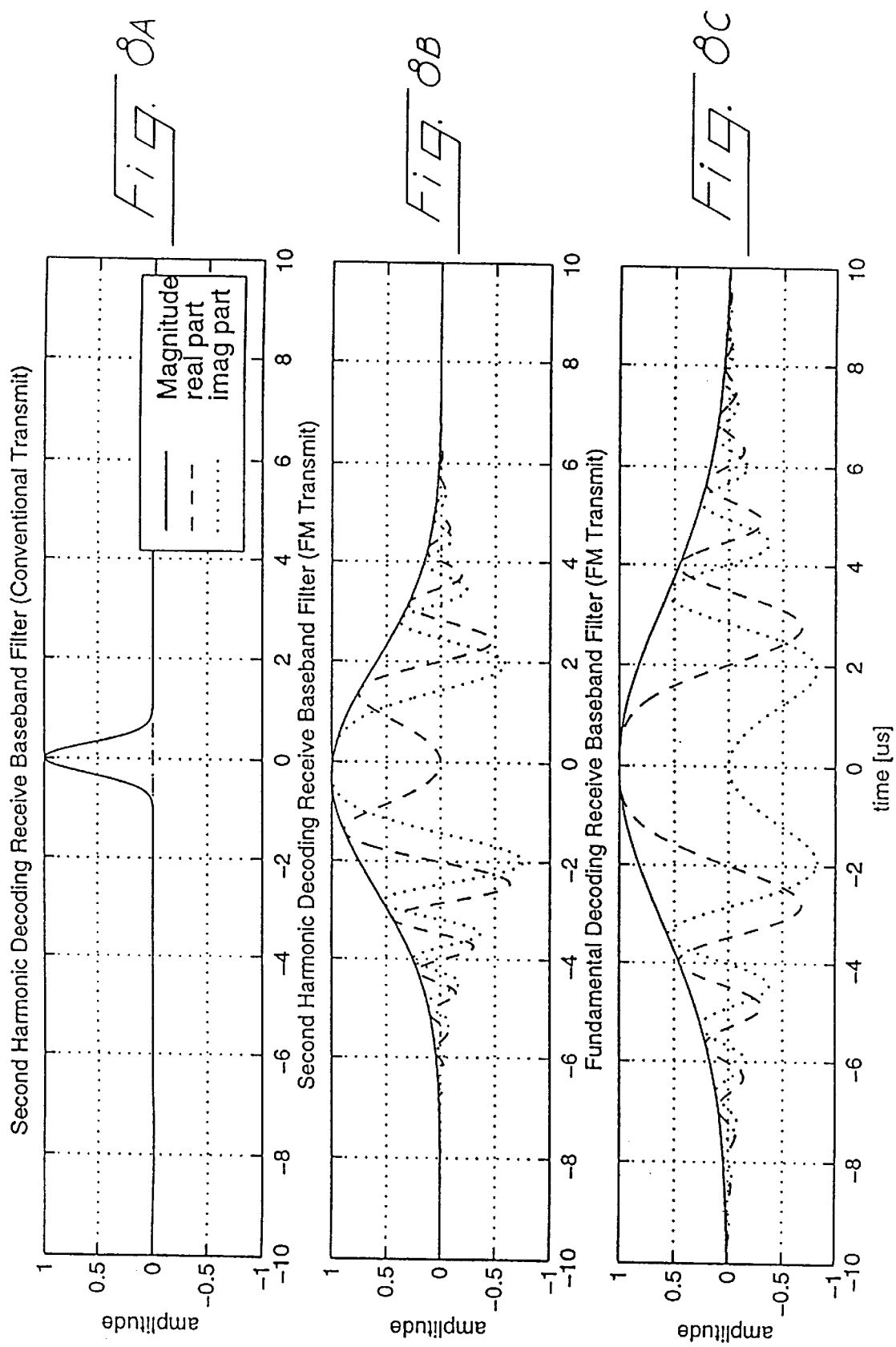

US 6,241,674 B1

MEDICAL ULTRASOUND DIAGNOSTIC IMAGING METHOD AND SYSTEM WITH NONLINEAR PHASE MODULATION PULSE COMPRESSION

CROSS REFERENCE TO RELATED APPLICATIONS

This application is related to co-pending U.S. Pat. application Ser. No. 09/283,746, filed Mar. 31, 1999, the entirety of which is hereby incorporated by reference.

BACKGROUND OF THE INVENTION

Ultrasonic images formed from harmonics generated from nonlinear propagation without the use of contrast agents have emerged within the medical ultrasound field as a valuable new diagnostic mode in medical imaging. A preferred tissue harmonic image is formed after listening for a second harmonic of the transmitted fundamental signals. The use of injected nonlinear contrast agents can also be used to further increase the signals from frequency bands other than the transmitted fundamental frequencies, such as the second harmonic of the fundamental or half the fundamental frequency, a subharmonic. Over the last few years there has been an increased interest in using injected nonlinear contrast agents for enhancing the diagnostic examination. More recently, the use of low amplitude excitation for the purposes of minimizing agent disruption, improving contrast between agent and tissue, and visualizing small blood vessels has generated increased interest.

Reduced clutter noise, reduced reverberation artifacts, and improved contrast have made tissue harmonic images preferred in difficult to image patients. Since the amount of tissue-generated harmonics can be substantially less than the fundamental, since harmonic energy is gradually accumulated from the face of the transducer, and since tissue attenuation is greater at higher frequencies, images generated from harmonic energy suffer from an inferior signal-to-noise ratio (SNR) as compared to images formed from fundamental energy alone. Hence, harmonic images can lack critical diagnostic information at shallow areas near the transducer face, at deep areas near the penetration limit of fundamental images, at outer edges of scan formats, and at large steering angles for individual ultrasound lines and individual transducer elements. Increased transmit voltages can increase returned signal levels and often SNR, but a maximum is reached based on practical electrical limits.

Imaging with low amplitude excitation while using injected contrast agents can minimize agent disruption, such as agent destruction, leaving more agent available for longer examination times and increased detection of small vessel flow. However, low amplitude excitation can produce unacceptably poor image quality where agent is not present or present in low concentrations. Further, contrast agent signals returns in the second harmonic frequency band and other bands such as the subharmonic and ultraharmonic frequencies may be limited by conventional transmit pulses. Since transmit voltages can not be increased without disrupting contrast agents, images with low amplitude excitation will exhibit poor SNR.

Frequency modulated (FM) pulse-compression is a well known technique for increasing the average power of a signal without increasing the instantaneous peak power. This technique was developed for radar applications in the 1940's and 1950's and more recently suggested in the medical ultrasound field for fundamental imaging (M. O'Donnell, Coded Excitation System for Improving the Penetration of Real-Time Phased Afray Imaging Systems, IEEE Transactions on Ultrasonics, Ferroelectrics, and Frequency Control, Vol. 39, No. 3, pp. 341–51, May 1992); and contrast agent imaging (Y. Takeuchi, Coded Excitation for Harmonic Imaging, Ultrasonics, PH-3, 1996.).

SUMMARY

A preferred embodiment described below implements a method for increasing the SNR by applying coded transmit pulses and pulse-compression receive filters to the tissue harmonic image formation process without the use of contrast agents and without a significant (or any) loss in axial detail resolution.

An apparatus that uses coded transmitted signals with a pulse-compression receive filtering technique that selectively operates on a returned harmonic signal from tissue may show more promise for improved SNR and reduced clutter noise as compared to an apparatus that uses the fundamental signal. In particular, tissue harmonic images inherently exhibit less penetration and lower SNR at the edges of the field-of-view, but often exhibit reduced clutter noise artifacts providing more diagnostic information when compared to conventional fundamental images. Thus, in certain imaging environments an increase in SNR and penetration in fundamental images may not increase the diagnostic information due to strong clutter noise artifacts, but a similar or equivalent increase in SNR in a tissue harmonic image may increase the diagnostic information.

Other preferred embodiments described below implement unique nonlinear phase modulation coding schemes for detecting integer or fractional harmonic energy with the use of contrast agents. Improved SNR and increased agent specificity may increase diagnostic information.

BRIEF DESCRIPTION OF THE DRAWINGS

FIGS. 2a, 2b, 2c and 2d are graphs of a conventional transmit pulse, an FM coded transmit pulse (time-bandwidth product equal to 4), transmit signal phase and transmit signal instantaneous frequency, respectively.

FIGS. 3a, 3b, 3c and 3d are graphs of a conventional tissue second harmonic signal associated with the transmit pulse of FIG. 2a, a tissue second harmonic signal associated with the transmit pulse of FIG. 2b, tissue signal phase and tissue signal instantaneous frequency, respectively. Also shown in FIGS. 3a and 3b are the envelopes of the tissue fundamental signals.

FIGS. 4a, 4b, 4c, 4d and 4e are graphs of a second harmonic decoding receive baseband filter for the receive pulse of FIG. 3a, a second harmonic decoding receive baseband filter for the receive pulse of FIG. 3b, a fundamental decoding receive baseband filter for the FM coded transmit pulse, decoding receive filter phases, and detected outputs, respectively.

FIGS. 6a through 6d correspond to FIGS. 2a through 2d, respectively, except that FIGS. 6b, 6c and 6d relate to a coded transmit signal having a time-bandwidth product of 8.

FIGS. 7a, 7b, 7c and 7d correspond to FIGS. 3a through 3d, respectively, except that FIGS. 7b, 7c and 7d relate to a tissue second harmonic signal associated with the transmit pulse of FIG. 6b.

FIGS. 8a through 8e correspond to FIGS. 4a through 4e, respectively, except that FIGS. 8b through 8e relate to fundamental and harmonic decoding filters and echo signals associated with the transmit signal of FIG. 6b.

DETAILED DESCRIPTION OF PRESENTLY PREFERRED EMBODIMENTS

To overcome the inferior SNR in harmonic images in comparison to fundamental images for those cases that are electrically-limited or MI-limited, but not limited by thermal constraints, spatial-peak-temporal-average limits, or otherwise, the transmitted signal can be lengthened (uncompressed or expanded) to increase the total energy. Later in the signal processing chain any order harmonic signal can be re-compressed to maximize axial detail resolution. This method effectively increases the time-bandwidth product by increasing the temporal duration of the transmitted signal while maintaining the over-all bandwidth (which is proportional to the axial detail resolution). The well-known technique of coded transmission and the unique receive filtering disclosed here can be combined to generate any order harmonic image to improve the diagnostic value of ultrasound images.

The preferred methods disclosed here can be used to improve the SNR in tissue harmonic imaging with or without contrast agents. In one preferred embodiment second harmonic imaging of tissue without the use of contrast agents improves the SNR, which translates into increased penetration and improved diagnostic information.

DETAILS OF OPERATION

Figure 1:
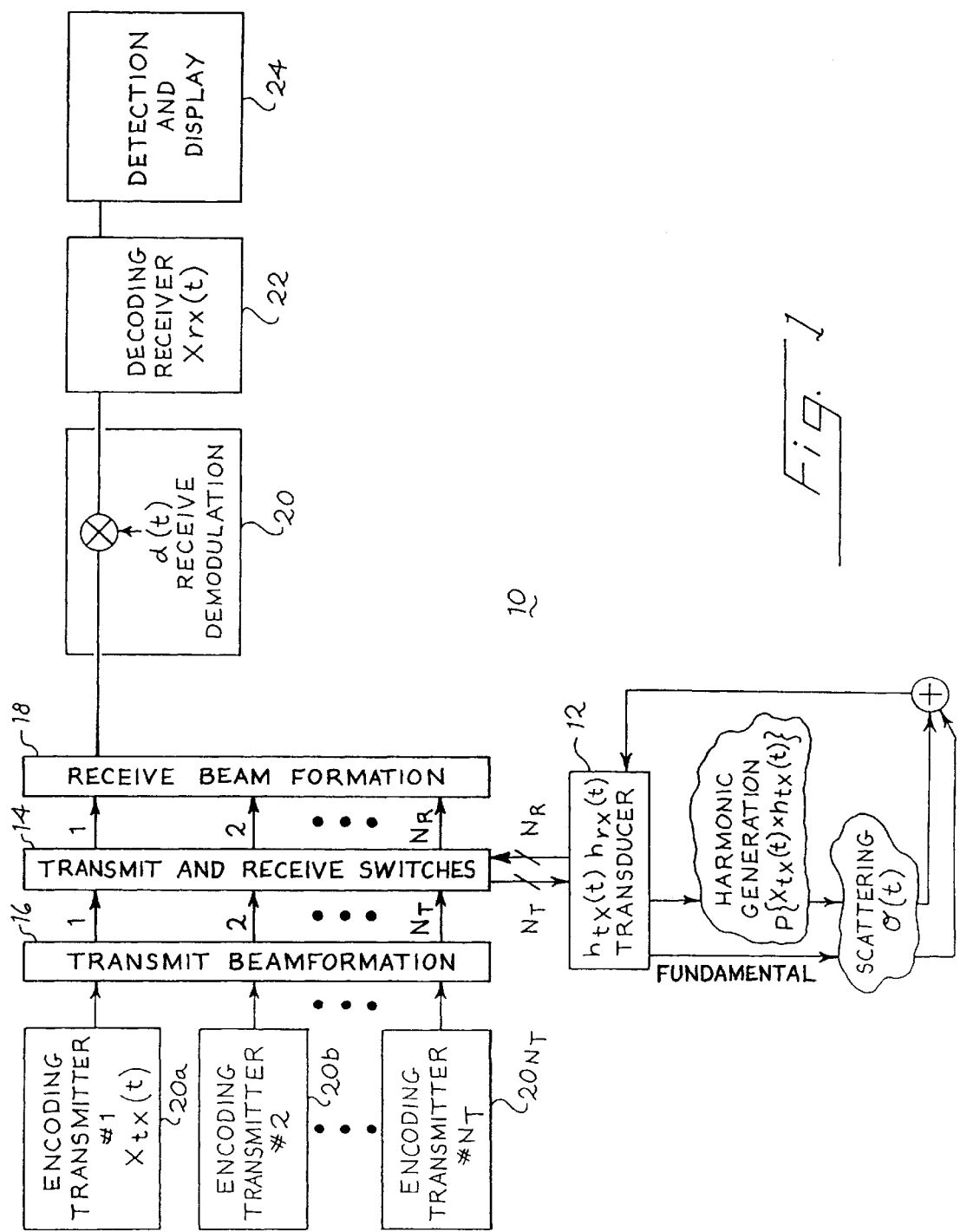
FIG. 1 is a schematic diagram of a medical diagnostic ultrasonic imaging system that incorporates a preferred embodiment of this invention.
Figure 2C:
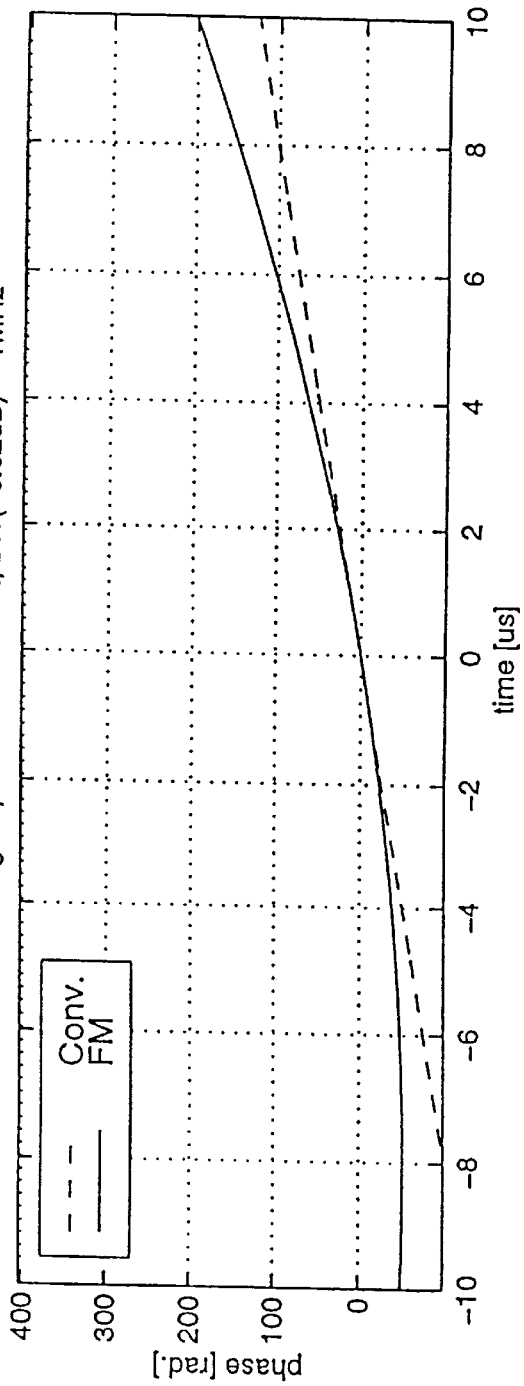
Figure 2D:
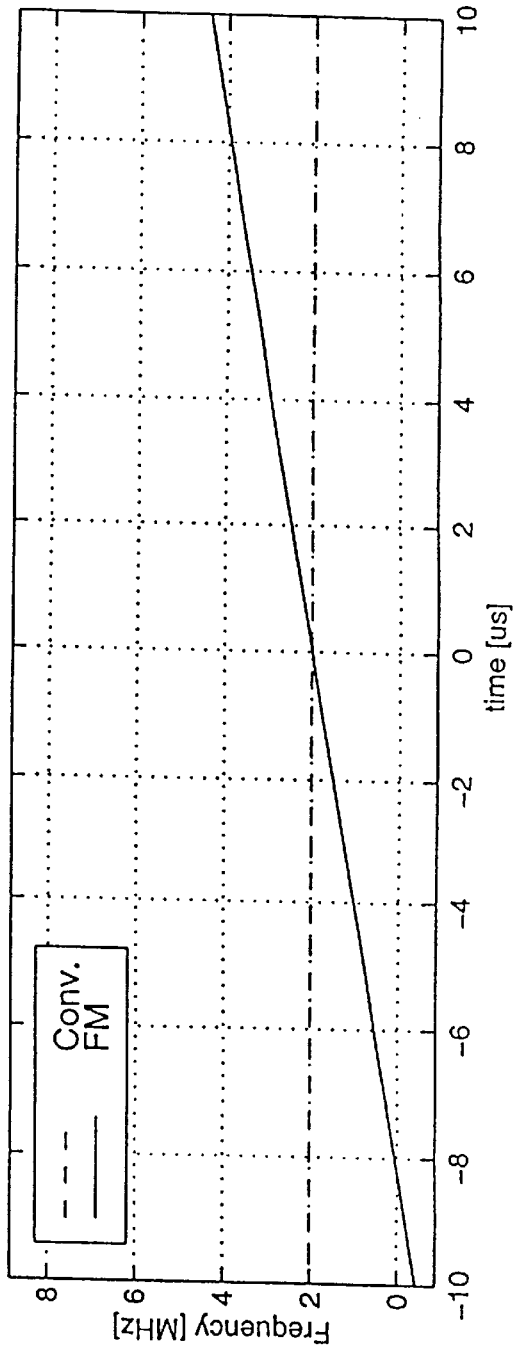

FIG. 1 is a block diagram for a medical diagnostic ultrasound imaging system that can be used to implement this invention. The imaging system 10 FIG. 1 includes a transducer 12 that in this embodiment is a one-dimensional, phased-array transducer. The transducer 12 includes an array of individual transducer elements that are coupled via transmit and receive switches 14 both to a transmit beamformer 16 and a receive beamformer 18. The transmit beamformer 16 receives as inputs coded transmit pulses from encoding transmitters 20a, 20b, ... 20Nt, and supplies suitable delays and/or phase changes to cause the coded transmit pulses from the transmitters 20a, 20b, ... 20Nt to produce ultrasonic signals from the associated transducer elements timed and phased to add coherently in a predetermined region of the tissue being imaged.

Similarly, the receive beamformer 18 supplies suitable time delays and/or phase changes to cause received echo signals from the individual transducer elements to sum coherently along a desired beam direction. The beamformed echo signals generated by the receive beamformer 18 are applied to a receive demodulator 20 that demodulates the echo signals to a desired frequency range. The demodulated echo signals are then applied to a decoding receiver 22 that applies a pulse-compression function to the beamformed, demodulated echo signals. The decoded echo signals are then applied to an image processor 24 for detection and display.

The following mathematical description, which ignores the contribution from tissue attenuation, acoustic diffraction, and the beam formation process, applies to the system of FIG. 1. The formation of an ultrasound line can be modeled as:

$$I(t)=[P\{X_{tx}(t)*h_{tx}(t)\}*\theta(t)*h_{rx}(t)]d(t)*X_{rx}(t) \quad (1)$$

where
$X_{tx}(t)$=transmit waveform
$h_{tx}(t)$=transducer voltage-to-pressure transfer function
$P\{...\}$=operator p models harmonic signal generation
$\theta(t)$=scatterer response
$h_{rx}(t)$=transducer pressure-to-voltage transfer function
$d(t)$=demodulation function
$X_{rx}(t)$=receive filter or pulse-compression decoding filter
t=time
*=convolution operation To increase the transmit energy without sacrificing axial detail resolution, the conventional transmit waveform $X_{tx}(t)$ with amplitude modulation a(t) and modulation frequency $f_m$ can be expressed as follows:

$$X_{tx}(t)=Re\{a(t)e^{j2\pi f_m t}\} \quad (2)$$

$X_{tx}(t)$ can be modified with a temporally dependent phase term $\phi(t)$. Note, "Re" stands for the real part of $\{...\}$. In general, the new transmit waveform is $$X^1tx(t)=Re\{a(t)e^{j\phi(t)}e^{j2\pi f_m t}\} \quad (3)$$

where $$\phi(t)=K_1 t^2+K_2 t^3+...+K_n t^{(n+1)} \quad (4)$$

and $K_i$ are arbitrary constants. Proper selection of $\phi(t)$ and a(t) allows a compact fixed-bandwidth temporal pulse with a time-bandwidth product of about one to be temporally expanded to greater time-bandwidth products allowing greater transmitted signal energy. After receiving scattered signals from tissue, a properly designed receiver can compress the temporally expanded pulse and restore a compact pulse. This process retains the preferred axial detail resolution associated with the specified bandwidth without significant degradation from the expanded transmit pulse. Excellent axial detail resolution is only maintained with the proper decoding receiver and adequate rejection of out-of-band frequency components. With proper decoding with a receiver designed to selectively listen for desired second, lower order, or higher order harmonic energy, the time-bandwidth product can be increased beyond the conventional value of about one, improving the SNR. As is well known in the art, a preferred decoder for fundamental imaging that may maximize SNR is a matched filter. Thus, after demodulation at the dominant fundamental frequency, the receiver decoder can be a scaled version of the time-reversed phase-conjugate of $$a(t)e^{j\phi(t)}.$$

For harmonic imaging, the preferred decoder is dependent on the order and mechanism of the harmonic signal generation. Again, a matched filter, matched to the harmonic of interest, is a preferred decoder. For second harmonic tissue imaging a reasonable model can be obtained by solving the well-known Riemann wave equation (*Nonlinear Acoustics*, Mark F. Hamilton, et al. ed, 1998, pg 75).

$$\frac{\partial g}{\partial t} + \frac{Co\partial g}{\partial z} = \left(\frac{Bg}{\rho_o C_o^2}\right)\frac{\partial g}{\partial t} \text{ for the pressure } g(t, z), \tag{5}$$

where
Co is the small signal sound speed
ρo is the ambient density
B is the parameter of nonlinearity,
by applying the boundary condition, or forcing function, equal to the transducer's transmit pressure signal at its face; i.e., $$g(t, z)\bigg|_{z=0} = f(t).$$

See, for example: page 75 of Nonlinear Acoustics, edited by Mark F. Hamilton and David T. Blackstock, copyright 1998.

Using straight-forward perturbation analysis (see for example: page 281, section 2 of Nonlinear Acoutics) the general model takes the form $$g(t, z) = f(t - z/Co) + Kt\frac{d[f^2(t - z/Co)]}{dt}, \tag{7}$$

which yields a second harmonic signal generated from the temporal derivative of the squared fundamental pressure signal, f(t), with Kt equal to the tissue material properties. An example of a model that may be applicable for contrast agent imaging of second harmonic energy excludes the temporal derivative, but is still dependent on the square of the fundamental pressure.

Using the general transmit waveform signal in eq. (3), the model operation ρ{ . . . }, and assuming the transducer's transmit transfer function has insignificant influence over the frequency band of interest, the generated second harmonic signal in tissue can be shown to be $$X_{2nd}(t) = D_i \text{Re}\{n(t)e^{j4\pi f_m t}\} + a(t)\frac{d[a(t)]}{dt}, \tag{8}$$

where $$n(t) = b(t)a^2(t)\left[\left[2\pi f_m + \frac{d[\phi(t)]}{dt}\right]\right]e^{j2\phi(t)}e^{j\theta(t)} \tag{9}$$

$$b(t) = \left[\frac{\left(\frac{d[a(t)]}{dt}\right)^2}{a^2(t)\left(2\pi f_m + \frac{d[\phi(t)]}{dt}\right)^2} + 1\right]^{1/2} \tag{10}$$

$$\theta(t) = \tan^{-1}\left\{\frac{a(t)\left(2\pi f_m + \frac{d[\phi(t)]}{dt}\right)}{\frac{d[a(t)]}{dt}}\right\} \tag{11}$$

Di=constant

Notice that the second harmonic signal has been effectively frequency modulated up by twice the original modulation frequency of $f_m$, i.e., $e^{j4\pi f_m t}$, and there is additional low frequency energy near DC due to the last term $$a(t)\frac{d[a(t)]}{dt}.$$

This last term appears because during nonlinear acoustic propagation signal peaks travel faster than signal troughs for a finite bandwidth signal; i.e., positive relative pressure (peaks) produce greater tissue sound velocities than negative relative pressure (troughs). For second harmonic imaging of contrast agents, $$n(t) = a^2(t)e^{j2\phi(t)} \tag{12}$$

After receiving the scattered tissue energy and appropriate per channel delay, phasing, and apodization are applied by a beamformer, the harmonic signals of interest can be demodulated to a desired frequency band for further processing. A preferred band is baseband. If the demodulation function d(t) is chosen centered at the second harmonic frequency, i.e., $$d(t) = e^{j2(2\pi f_m t)} \tag{13}$$

and $X_{rx}(t)$ is chosen to be equal to $Y^*_{2nd(-t)}$
where $$Y_{2nd}(t) = b(t)a^2(t)\left[\left[2\pi f_m + \frac{d[\phi(t)]}{dt}\right]\right]e^{j2\phi(t)}e^{j\theta(t)} \tag{14}$$

for tissue second harmonic energy, or $$Y_{2nd}(t) = a^2(t)e^{j2\phi(t)} \tag{15}$$

for contrast agent second harmonic energy, and * is the complex conjugate operation, then a preferred embodiment that maximizes the SNR and maintains excellent axial detail resolution can be realized. In this preferred embodiment, a matched filter, which may maximize the SNR, is used for the pulse-compression receiver $X_{rx}(t)$. A conventional receiver would lack the decoding and additional nonlinear phase modulation necessary to restore the desired axial resolution. After demodulation, the preferred pulse-compression matched receiver is a time-reversed phase-conjugate of $$n(t) \tag{16}$$

where the demodulation signal processing step effectively shifts the frequency band to a preferred frequency band. The matched filter, or more generally the pulse compression filter, can effectively suppress the low frequency term near DC and the fundamental energy or other undesired energies. Amplitude modulation in the receiver other than a matched filter envelope may also be used if desired. In particular, additional pulse shaping may be used to help suppress unwanted range lobes.

Example

The following is an example of a nonlinear quadratic phase modulated (PM), linear frequency modulated (FM) chirp pulse-compression code for second harmonic tissue imaging. The transmit signal has the following characteristics:

1) The amplitude is modulated with a Gaussian envelope of temporal duration:

$$T=(\alpha)^{-1/2} \quad (17)$$

where the duration is defined by the −6.82 dB amplitude below the peak;

2) The frequency bandwidth at the −6.82 dB level below the peak is $$W = \left(\frac{\alpha^2 + \gamma^2}{\alpha}\right)^{1/2}; \quad (18)$$

3) The time-bandwidth product is defined as:

$$TW = \left(1 + \left(\frac{\gamma}{\alpha}\right)^2\right)^{1/2}. \quad (19)$$

The general transmit signal is $$X^1_{tx}{}^1 = Re\{e^{-\pi\alpha t^2} e^{j\pi\gamma t^2} e^{j2\pi f_m t}\} \quad (20)$$

and for a specified bandwidth W (i.e. axial detail resolution) and desired pulse duration T, the instantaneous frequency in radians per second is $$\hat{\omega} = 2\pi(\gamma t + f_m) \quad (21)$$

Using eq. (13) above for this example, the receive pulse-compression matched filter after demodulation at the second harmonic frequency is $$X_{rx}(t) = D_2 \left[\frac{\alpha^2 t^2}{(f_m - \gamma t)^2} + 1\right]^{1/2} \quad (22)$$

$$|f_m - \gamma t| e^{-2\pi\alpha t^2} e^{-j2\pi\gamma t^2} e^{j\tan^{-1}[(f_m - \gamma t)/\alpha t]},$$

where $D_2$ is a constant. A reasonable approximation for typical time-bandwidth products that can be obtained with current medical ultrasound systems is $$X_{rx}(t) = jD_3 e^{-2\pi\alpha t^2} e^{-j2\pi\gamma t^2} \quad (23)$$

where $D_3$ is a constant. Note, the time-bandwidth product for a clinical system will likely be determined by Ispta limits, thermal limits, and per channel electrical power. FIGS. 2 through 9 are examples of the signals at different stages in a system implementation. FIGS. 2 through 5 are representative of a system with a time-bandwidth product of 4, while FIGS. 6 through 9 are representative of a system with a time-bandwidth product of 8; i.e., the transmit signal temporal length used to produce the latter four figures was twice the transmit signal length used to produce the former four figures. The transmitted bandwidth for the two sets of four figures were identical. In general, systems with time-bandwidth products less than 50, more preferably less than 20, and most preferably less than 10 are preferred.

Description of FIGS. 2 Through 9

In the examples of FIGS. 2–9, the transmit modulation frequency is 2 MHz and the frequency bandwidth is 1 MHz. FIGS. 2a and 6a show a conventional transmitted signal, and the corresponding transmit envelope, in each figure without a time-dependent, nonlinear phase modulation; these two conventional transmit signals are identical and are shown in each case as a reference. FIGS. 2b and 6b each show a quadratic PM or linear FM coded transmit signal, and the corresponding transmit envelope. The peak signal levels are identical in all four figures, as would be typical based on electrical limits or desired spatial peak acoustic limits. FIGS. 2c and 6c show the linear transmit phases for the conventional and nonlinear phases for the coded signals, as shown in the preceding figures. FIGS. 2d and 6d show the instantaneous frequencies corresponding to the transmit phases as determined by the temporal derivative of these phases. Notice that the coded transmit signal phases are distinctly different from the conventional transmit signal phases and are nonlinear.

Figures 3C, 3D:
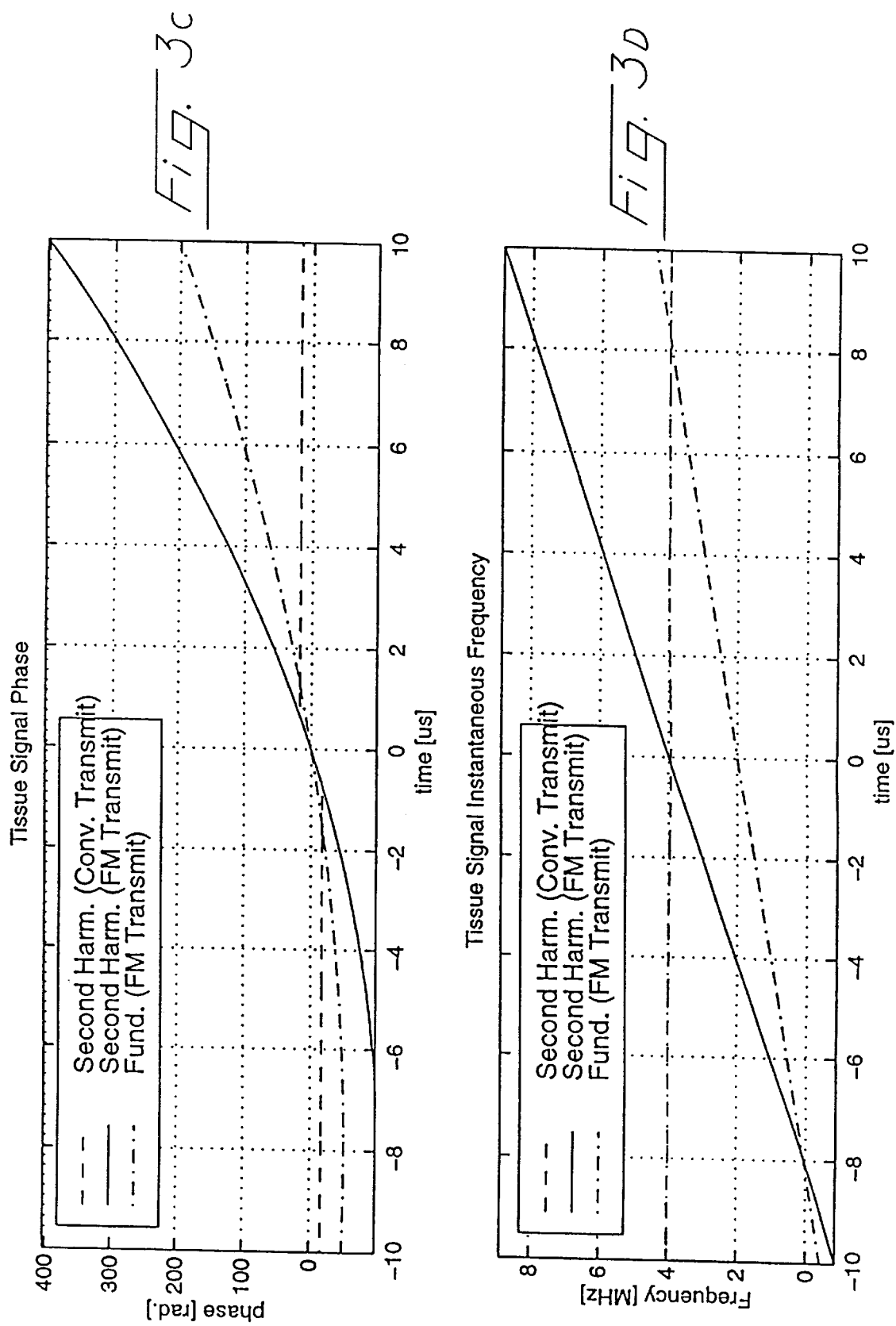
Figure 4D:
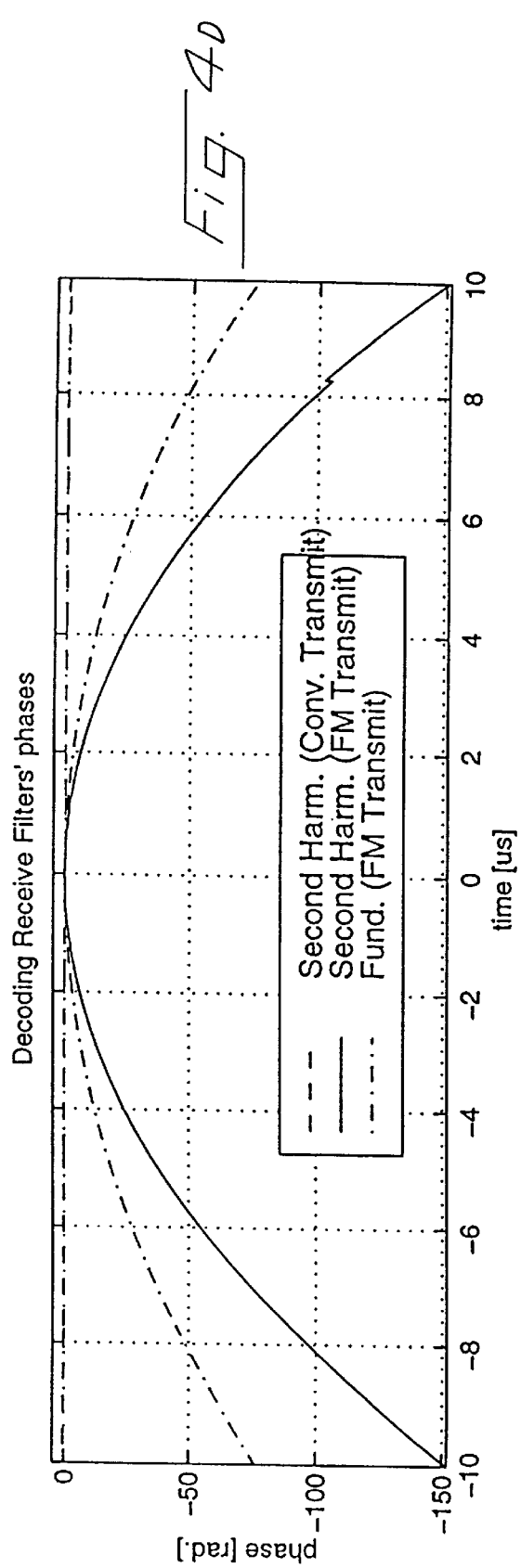
Figure 4E:
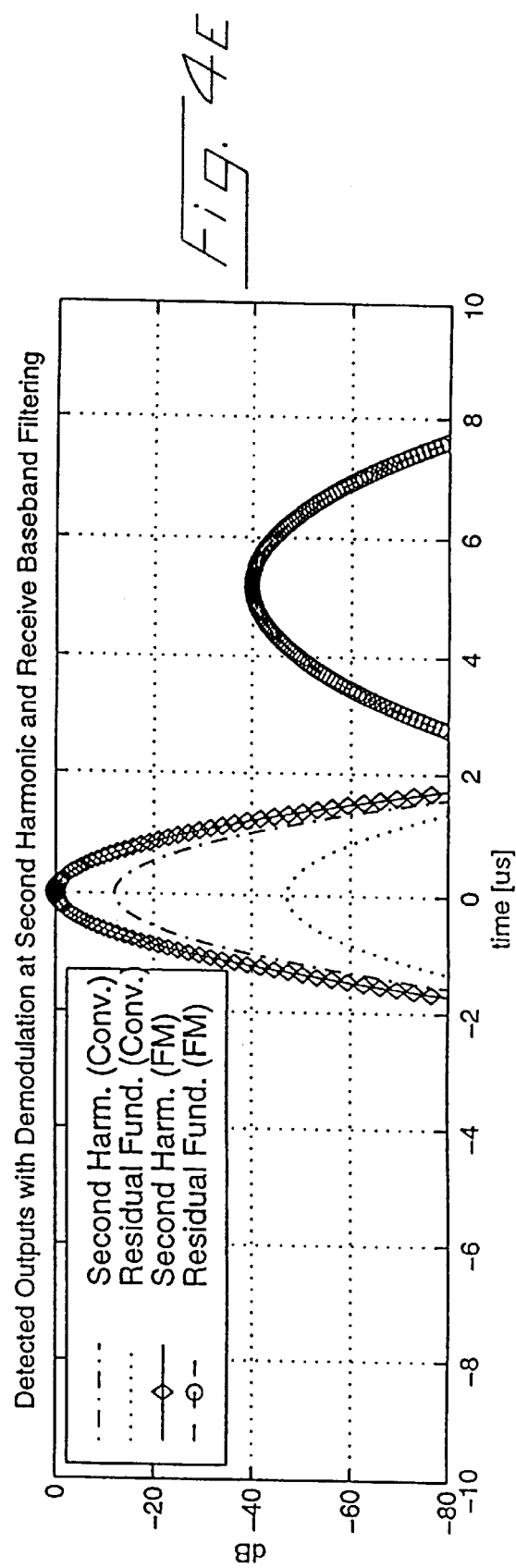
Figures 8D, 8E:
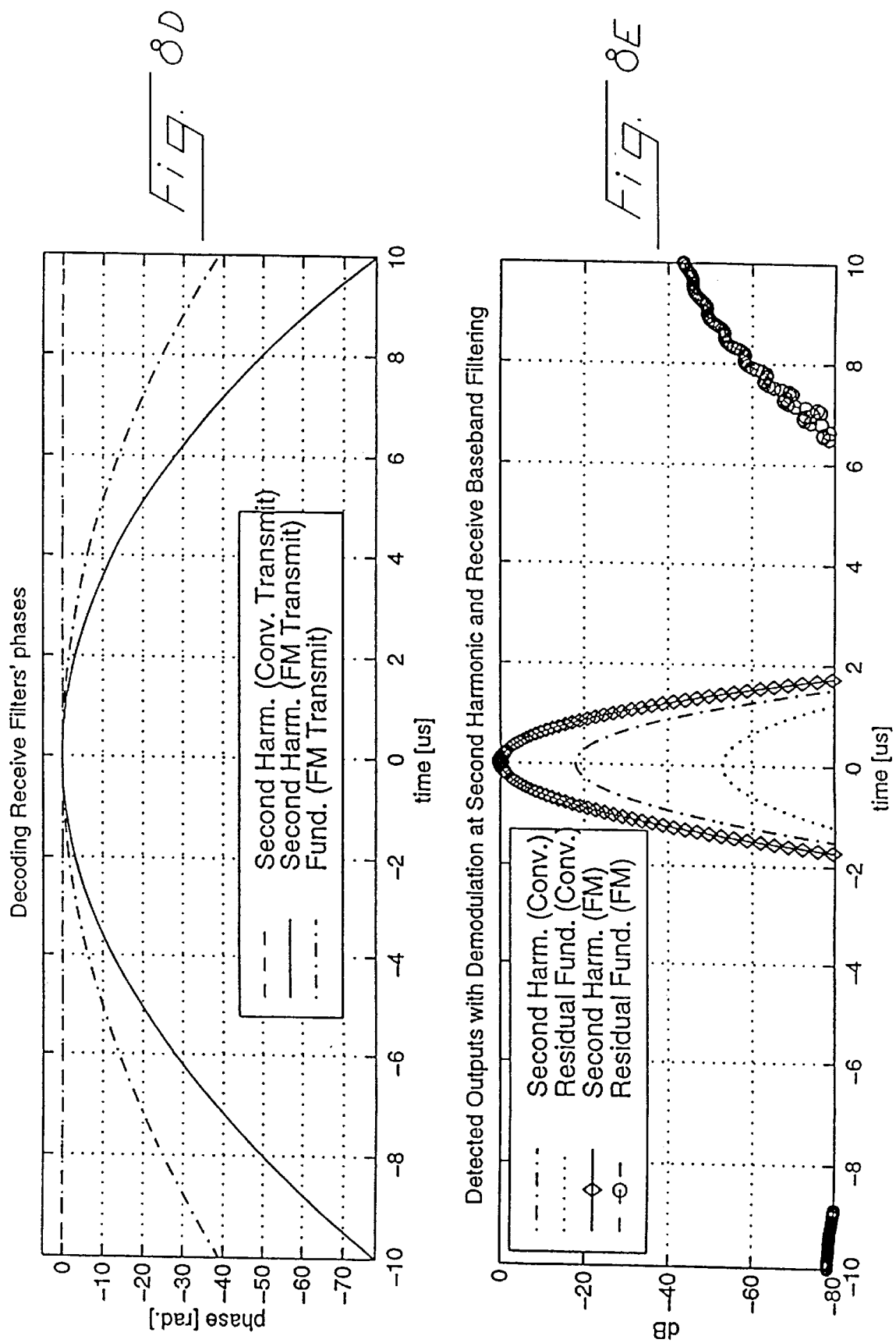

FIGS. 3a and 7a show the tissue second harmonic signal and its envelope associated with the conventional transmit signal where tissue attenuation and acoustic diffraction have been excluded. Also the tissue fundamental signal envelopes are shown for reference in these figures. Notice that the second harmonic signal provides improved axial detail resolution. FIGS. 3b and 7b show the tissue second harmonic signal and its envelope associated with the respective coded transmit signal. Again, these figures show the tissue fundamental signal envelopes for reference. FIGS. 3c and 7c show the tissue signal phases for the second harmonic signal with the conventional transmit signal, the second harmonic signal with the coded transmit signal, and the fundamental signal with the coded transmit signal. FIGS. 3d and 7d show the instantaneous frequencies corresponding to these tissue signal phases. Notice that the tissue signal phases and instantaneous frequencies for each type of tissue signal and each type of transmit signal are unique. It is necessary to take these differences into account when designing an optimized pulse-compression (or decoding) receive filter. In particular, the phase varies twice as fast as a function of time for the tissue second harmonic signal as compared to the tissue fundamental signal when coded transmit signals are launched from the transducer. FIGS. (4a, 4b, 4c) and (8a, 8b, 8c) show the pulse-compression, or decoding, receive baseband filter components for filtering second harmonic and fundamental received signals. In each of the two sets, the three figures show the second harmonic decoding filter with a conventional transmit signal, the second harmonic decoding filter with a coded transmit signal, and the fundamental decoding filter with a coded transmit signal, respectively. The latter of each set of three figures is provided for comparison and would be typical for imaging tissue with fundamental signals. Each figure shows the real part, the imaginary part, and the magnitude of each filter's response. Notice that the receive decoding filter for the second harmonic signal is different from the receive decoding filter for the fundamental signal when coded transmit signals are launched from the transducer. These differences are also seen by plotting the phase of the receive filter as a function of time. FIGS. 4d and 8d show these phases for the three different types of filters. Note that the phases change twice as fast as a function of time for the second harmonic as compared to the fundamental when coded transmit signals are employed. For imaging of higher or lower order harmonics the instantaneous phase of the decoding filter preferably matches the desired harmonic phase changes. For example, a subharmonic of order ½ would be preferentially decoded with a filter whose phase changes at half the rate as the transmitted signal's phase. FIGS. 4e and 8e show the final output signals after proper demodulation at the dominant second harmonic frequency (4 MHz), baseband receive filtering with a second harmonic pulse-compression filter (from FIGS. 4a or 4b and FIGS. 8a or 8b, respectively, for the two cases), and display detection. Notice the following:

1) The axial resolutions, as defined by the width of the output signals, for the two second harmonic signal processing techniques are identical. With coded transmit signals and proper receive filtering the axial detail resolution is maintained.
2) The energy in the second harmonic returned signal associated with the coded pulse-compression technique is greater than the returned energy associated with the conventional, non-coded, technique. Additional energy was made available by the temporally expanded transmit waveforms. Notice that the difference in returned detected signal energy between the two separate cases (case 1 with time-bandwidth product=4 and case 2 with time-bandwidth product=8) is greater for the larger time-bandwidth product of 8, as expected.
3) There exists a residual fundamental signal for both signal processing techniques, coded and non-coded, due to imperfect suppression of fundamental energy. The coded signal processing technique effectively shifts in time the dominant residual energy with respect to the conventional, noncoded, signal processing technique. This residual energy will be insignificant in a clinical setting for appropriately selected signal bandwidths. Larger bandwidths will generate less fundamental suppression due to frequency spectral overlap. Poor fundamental energy suppression or unacceptable residual fundamental energy can further be reduced with proper summing or filtering of pre-detected received pulses associated with different transmitted envelope phases. The combination through simple addition or filtering of multiple received pulses can effectively accentuate the desired harmonics of interest while cancelling undesired fundamental or other harmonic energy. For example, two pulses transmitted with opposite phases (i.e., 0 and 180 degrees) in the same direction can be added after the pulse-compression receive filter to suppress fundamental signals while at the same time increasing the usable axial detail resolution and SNR of the second harmonic signals. In another example, two pulses with different initial envelope phases may be transmitted along different directions or from different origins and subsequently added after receiving and decoding with the pulse-compression filter. The non-collinear paired transmit pulses allow improved frame rates compared to the collinear transmit pulses with improved SNR due to the phase and amplitude modulation coding and decoding. In FIGS. 4e and 8e these multiple pulse combinations would reduce the signal energy in the residual fundamental signals.

Figure 5:
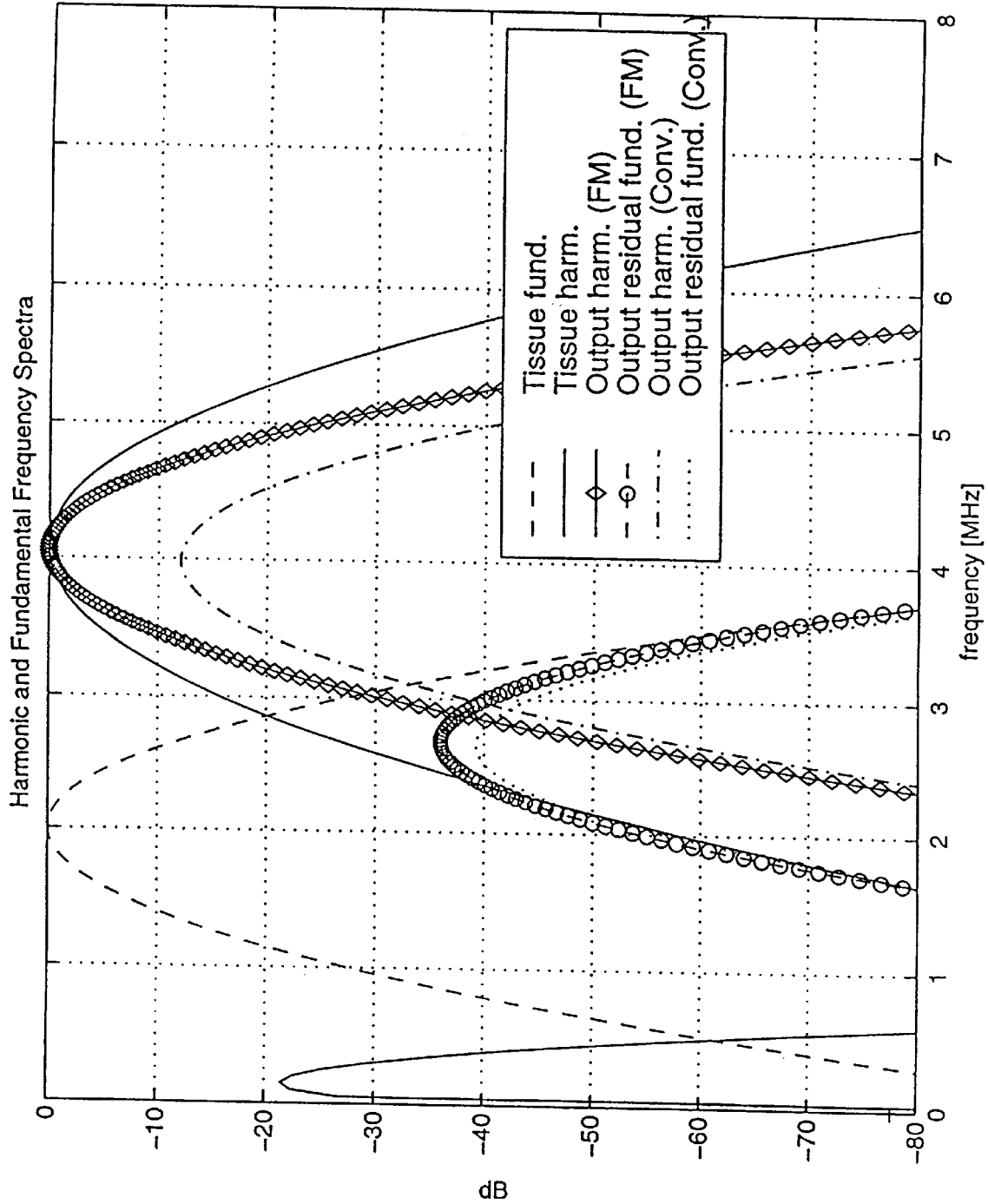
FIG. 5 is a graph of harmonic and fundamental frequency spectra.
Figure 6C:
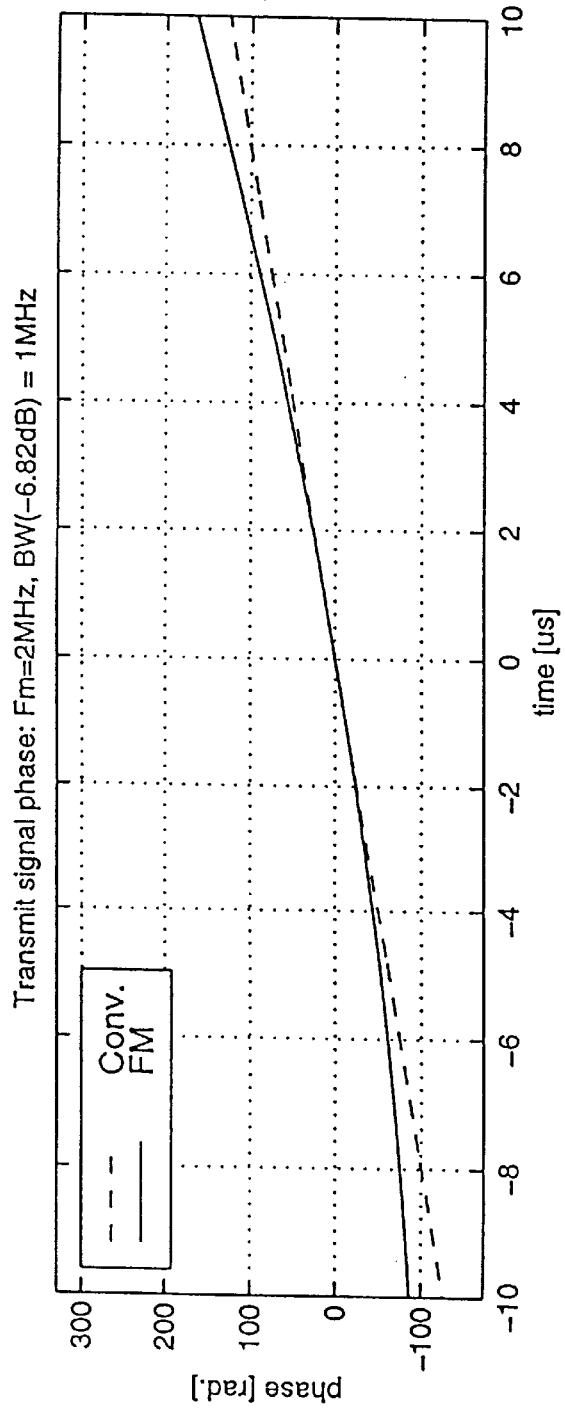
Figure 6D:
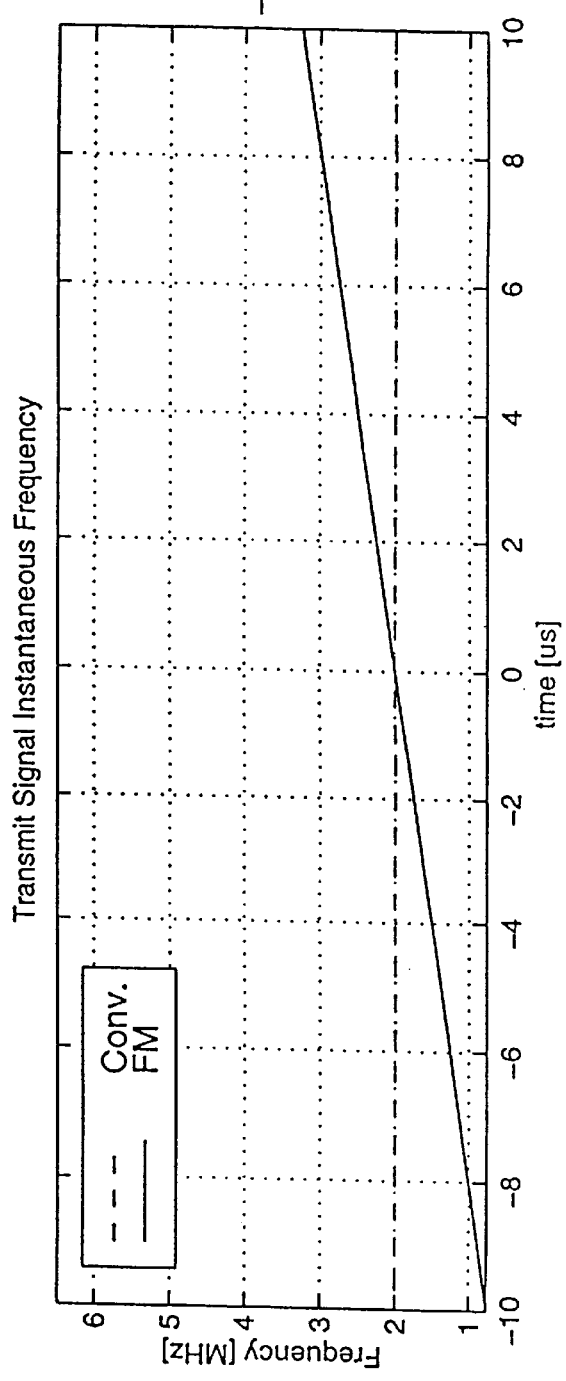
Figure 9:
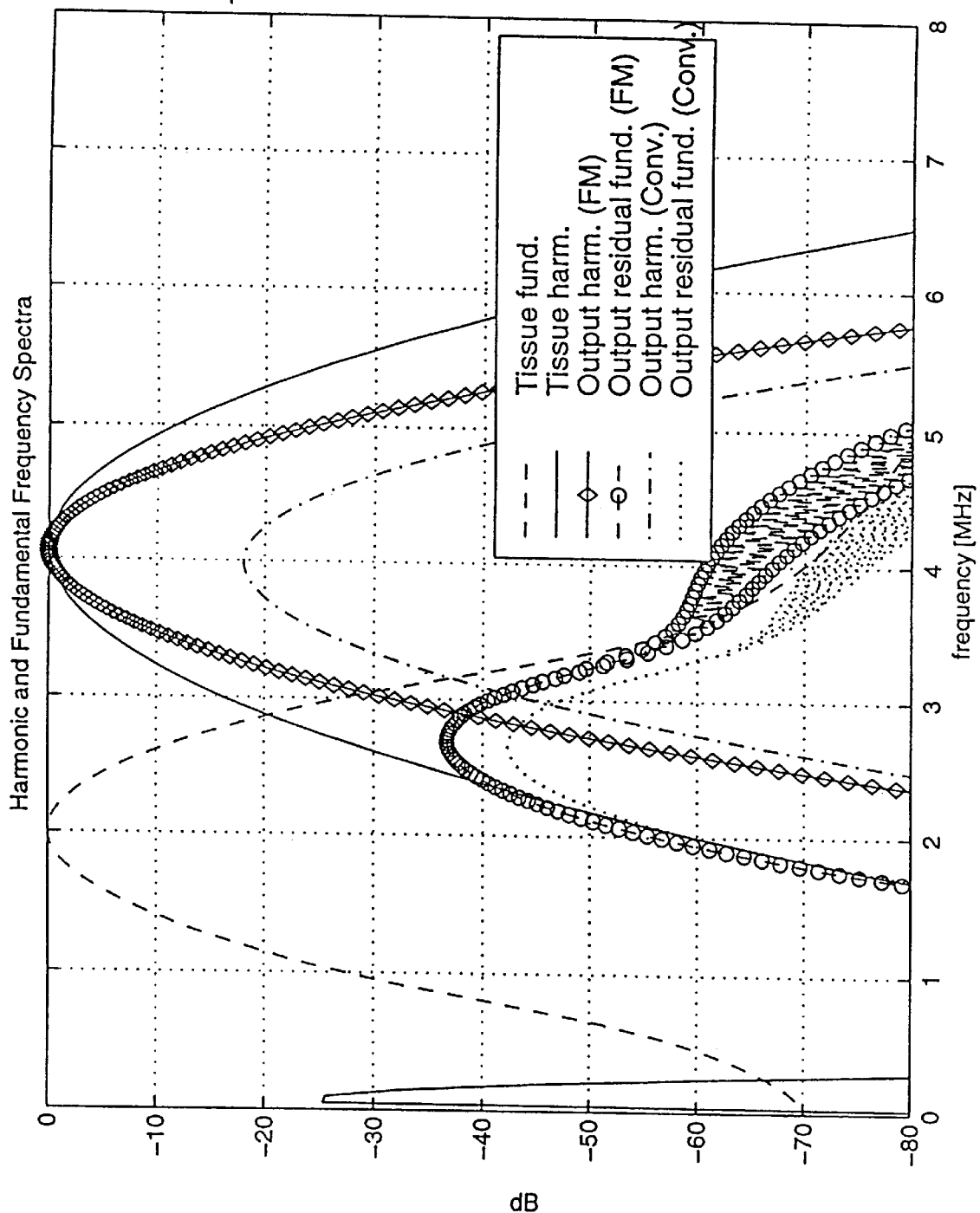
FIG. 9 corresponds to FIG. 5, except that the coded pulse is that of FIG. 6b.

FIGS. 5 and 9 show the tissue and detected output signals in the frequency domain for the conventional and coded transmit signals. These figures illustrate that the −6.82 dB bandwidths of the tissue fundamental and the tissue second harmonic signals remain constant, independent of the specified temporal duration of the transmitted signals. Also, the difference in detected signal energy for the returns from the coded transmit signals as compared to the returns from the conventional transmit signals is shown for the two cases. Although the output signal for the larger of the two time-bandwidth products would be greater for identical peak transmit signal levels between the two coded cases presented, all spectra in FIGS. 5 and 9 have been normalized for each case independently by the harmonic tissue signal peak for the coded pulse-compression technique. Thus the maximum spectral amplitude for the signal outputs is always zero decibels. This normalization emphasizes the differences in the tissue harmonic signal levels for conventional transmit signals and the residual fundamental signal levels after harmonic receive filtering.

Many modifications to the preferred embodiment and to the foregoing example are possible, including the following:
1) General modulation of amplitude, $\alpha(t)$, and phase, $\phi(t)$.

Figure 10:
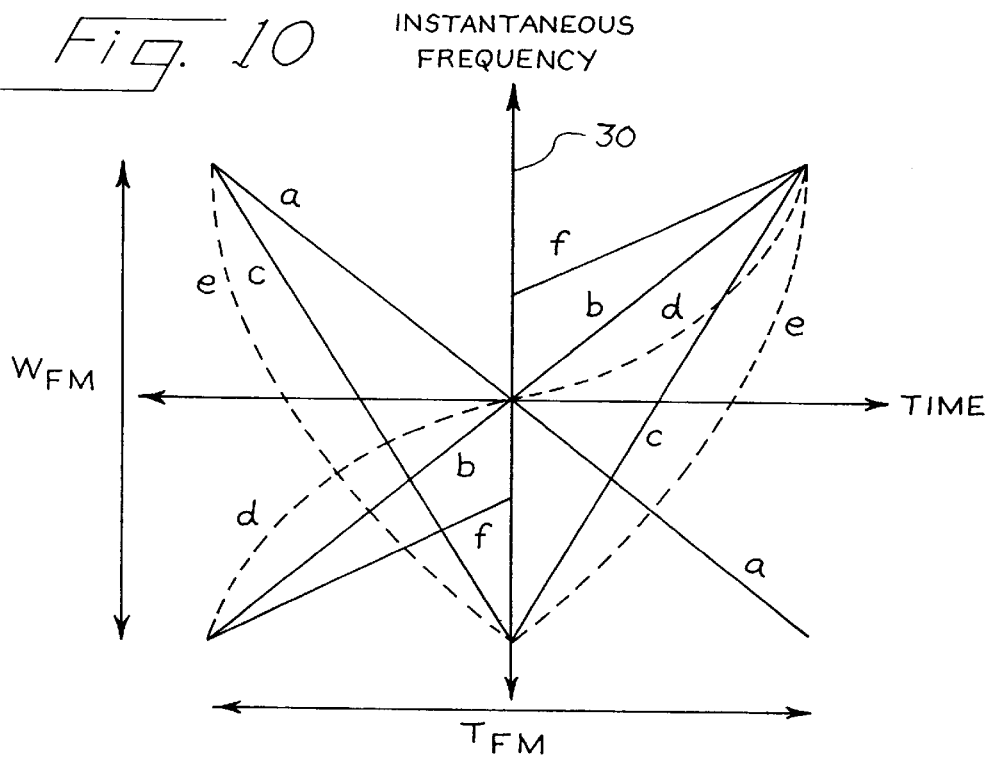
FIG. 10 is a diagram of alternative frequency modulation functions versus time that can be used to form coded transmit signals and/or pulse-compression receive filters in alternative embodiments.

An example of a Gaussian amplitude modulated envelope with nonlinear quadratic phase (or linear frequency) modulation versus time was given above, but many different types of amplitude and phase modulation functions can be used in the transmitter and in the pulse-compression receive filter. FIG. 10 shows a few examples of linear, nonlinear, discrete, and continuous instantaneous FM functions versus time. These functions are the temporal derivative of the phase modulation (PM) functions. The functions are preferably defined within the scope of the pulse temporal duration $T_{FM}$ and the desired frequency span $W_{FM}$. Note, the line 30 is situated at one-half the envelope duration. These are examples and are not exhaustive. Examples of linear FM (quadratic PM) functions are shown labeled a, b, and c. Two piecewise linear FM functions are functions f and c. Two nonlinear FM functions are labeled d and e. Note that the modulation functions c and e are symmetric about the line 30 while the other functions are asymmetric about line 30.

Figure 11:
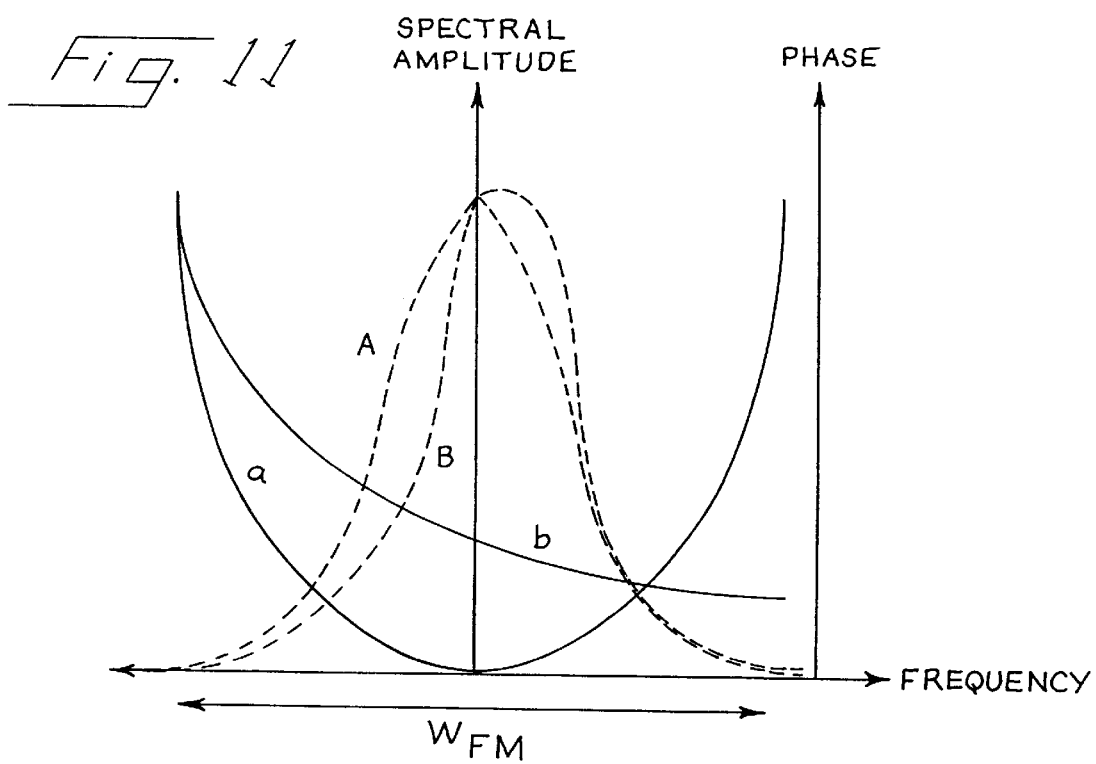
FIG. 11 is a diagram of alternative phase functions versus frequency and signal spectra that can be used in alternative embodiments.

FIG. 11 shows a few examples of symmetric and asymmetric nonlinear phase functions versus frequency together with general signal amplitude spectra. Spectra A and B, shown as dashed lines, are representative of signal spectra at the transmitter or input of the pulse-compression filter. Phase functions, a and b, shown as solid curves are examples of symmetric and asymmetric functions. Function a is symmetric about amplitude spectrum A or asymmetric about amplitude B. Function b is asymmetric about amplitude spectrum A and B.

Figure 12:
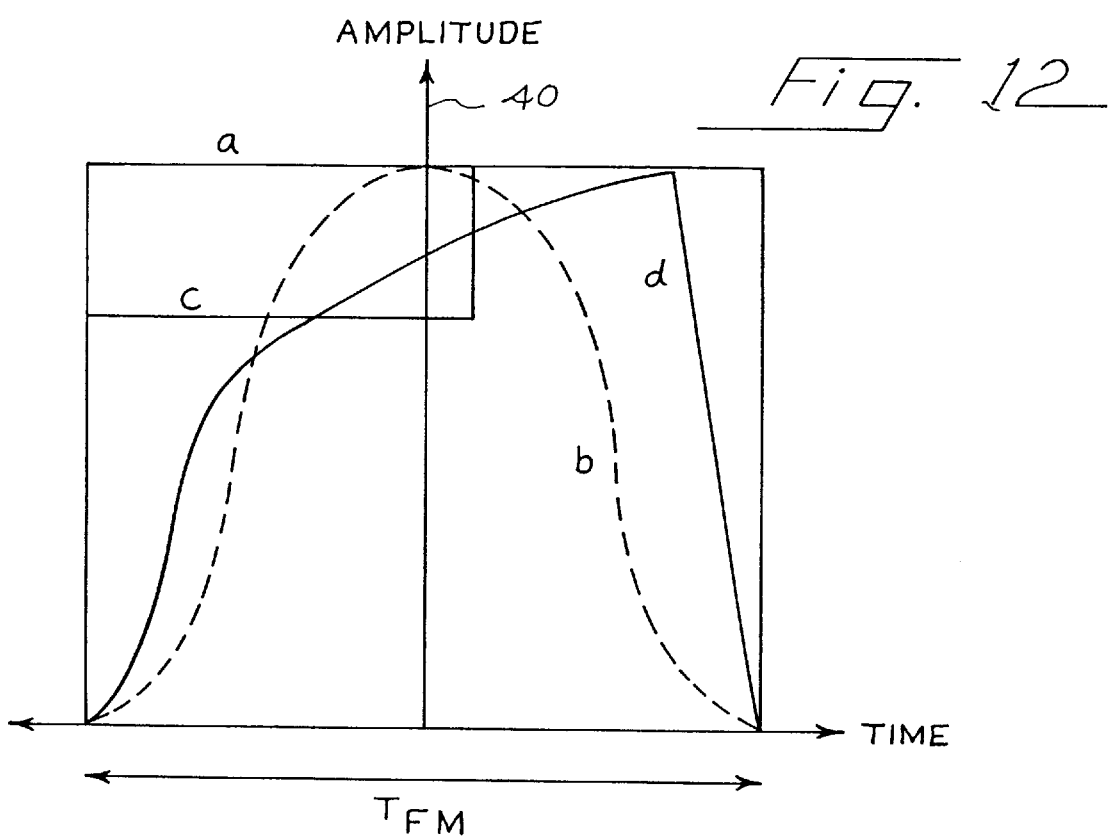
FIG. 12 is a diagram of alternative amplitude modulation functions versus time that can be used in alternative embodiments.

FIG. 12 shows a few examples of symmetric and asymmetric amplitude modulation functions versus time with respect to the line 40 located at one-half the envelope duration. Functions a and b are symmetric amplitude profiles while functions c and d are asymmetric profiles. These types of functions can be applied independently in the transmitter and pulse-compression receiver depending on the desired system over-all spectral response. Asymmetric functions are particularly useful to maximize SNR by compensating for spectral shaping created by tissue attenuation, acoustic diffraction, and impulse responses from system and transducer designs.

Some of these combinations illustrated in FIGS. 10, 11, and 12 may be preferred for specific system designs. Examples are given below.

1a) Phase modulation functions other than those that vary linearly or quadratically versus time such as nonlinear instantaneous frequency modulation functions may be preferred when constant amplitude pulses, such as function a in FIG. 12, are transmitted. The use of quadratic phase modulation (or linear FM) with constant amplitude modulation may produce clinically unacceptable range lobes, but amplitude modulation functions other than constant amplitude may not be available in the transmitter. Constant or uniform amplitude modulation is popular among commercial ultrasound manufacturers due to the reduced cost of these types of transmitters as compared to more sophisticated transmitters with non-uniform amplitude modulation such as the Programmable Waveform Generator (PWG) sold by Acuson Corporation under the tradename Sequoia. With constant amplitude modulation, nonlinear FM may be used to preferentially shape the pulse-compression output spectra to help suppress high range lobes. The unwanted range lobes can alternatively or further be reduced by proper non-uniform symmetric or asymmetric amplitude modulation in the pulse-compression receiver. The potential disadvantage to non-uniform amplitude modulation in the receiver is lost SNR. Nonlinear FM can eliminate the need for additional receive amplitude modulation and thus maximize SNR with constant amplitude transmitted pulses.

1b) Another example where uniform amplitude modulation may actually be preferred and nonlinear FM used, irrespective of the types of amplitude modulation available in the transmitter, is for near field harmonic imaging. Imaging near the face of the transducer places a limit on the expanded pulse lengths since receive circuitry can not be turned on until the transmitters have been turned off, at least for systems that use the same transducers to transmit and receive ultrasonic energy. Also, the SNR may be poor if harmonic energy is generated solely from tissue nonlinear propagation. If maximum energy is to be transmitted into the tissue over the shortest window of time, a uniformly amplitude modulated waveform is preferred. To maintain acceptable range lobe levels nonlinear FM may be used.

1c) The phase modulation function may be randomized which, again, can be beneficial for those systems constrained to uniform amplitude modulation. By controlling the instantaneous frequency of the transmitted waveform, the time between the signal zero crossings can be precisely controlled to generate pseudo-random sequences. After receive filtering with the matched filter response, a temporally compact output is produced which yields excellent axial detail resolution and improved SNR. Further, if range lobes are unacceptable and nonuniform amplitude modulation is not available, a second complementary transmit firing, with the expected loss in frame rate, may be used to accentuate the main temporal lobe of the output signal while generating secondary range lobes with polarities opposite to those associated with the initial transmit firing. These two separate outputs can be added before display processing to help suppress the unwanted range lobes since the opposite polarity range lobes will cancel. An example of these types of complementary codes is the Golay codes described in M. J. E. Golay, *Complementary Series,* IRE Transactions on Information Theory, Volume IT-7, Number 4, October, 1961.

Two important aspects should be noted about the application of various forms of these types of codes to harmonic imaging, such as binary codes, which may include Golay codes or the well known Barker codes. First, in order to produce an inverted version of a second harmonic pulse, as is required for most of these codes, the fundamental transmit pulse must be shifted by plus or minus 90 degrees. For example, to realize second harmonic signals of the form $$Re\{a^2(t)e^{j2\pi 2f_m t} - (a^2(t-T)e^{j2\pi 2f_m(t-T)})\}$$

and $$Re\{a^2(t)e^{j2\pi 2f_m t} + (a^2(t-T)e^{j2\pi 2f_m(t-T)})\}$$

where T is the time between the two pulses for this two pulse example, the transmitted signals should have approximate form $$Re\{a(t)e^{j2\pi f_m t} + j(a(t-T)e^{j2\pi f_m(t-T)})\}$$

and $$Re\{a(t)e^{j2\pi f_m t} + (a(t-T)e^{j2\pi f_m(t-T)})\}$$

Second, since the harmonic signal is generated by a nonlinear process, the two components of the transmitted signal should be sufficiently separated in time by time T to minimize overlap. Otherwise, a third undesired cross-product term would appear in the harmonic signals. By way of explanation, the harmonic waveforms shown above are examples of coding using complementary Golay codes. In addition, the first of the two waveforms is an example of a transmit waveform coded using the simplest Barker code of size two.

1d) Asymmetric phase functions versus frequency, i.e, functions like function b in FIG. 11, may be preferred for maximizing the SNR while maintaining accurate decoding in the pulse-compression receiver. Since frequency dependent attenuation preferentially attenuates higher frequency components more than lower frequency components, a receiver that tracks the returned spectral energy both in spectral width and center frequency can maximize SNR. One method to selectively position the depth-dependent spectral energy within a given baseband filter is to vary the demodulation frequency as a function of depth. If the SNR is to be maximized without unwanted image artifacts while varying the demodulation frequency, the receive filter can incorporate asymmetric phase functions and vary the filter impulse response with depth. This dynamically varying receive filter may be preferred.

If a depth-dependent receive filter is not available, other methods may be used to minimize inaccurate decoding or image artifacts with a fixed receiver.

One method is to fix the demodulation frequency to be constant with depth and keep the phase functions symmetric about a specific frequency, such as the transmit modulation frequency.

Another alternative, in particular for quadratic phase modulation, is to temporally delay the receive signal as a function of depth before it is filtered with the pulse-compression function. Increasing delays are added with increasing depths to maintain accurate decoding.

Yet another alternative is to maintain a symmetric, depth-independent, phase function with a depth dependent demodulation frequency and accept the possible artifacts. For some phase functions or corresponding FM functions the image artifacts may be tolerable.

1e) A transmitted pulse with temporally discrete segments with each segment consisting of independent amplitude and nonlinear phase modulation functions may be preferred. An example with this type of characteristic was given in FIG. 10 labeled function f. Function f incorporates two independent nonlinear quadratic PM functions (or piecewise linear FM functions as shown). This type of code that effectively consists of subcodes can be used to extract information from the tissue at two closely spaced time intervals or used to preferentially excite contrast agent harmonics. One temporal segment with a unique amplitude and phase function may preferentially excite or nucleate a mode of vibration that depends on the existence of the other coded segment. This type of code can be used to optimally detect fractional harmonic energy such as subharmonics. Of course multiple codes can be designed to overlap in time, which is effectively the addition of two codes. In this example with two different segments, the pulse-compression receiver can decode the energy associated with one or both segments. If one segment was used to excite a specific vibration mode, another segment can be used for imaging presentation. A specific example where these types of codes can be useful is where a low amplitude transmitted subharmonic is used to nucleate the growth of subharmonic energy from higher amplitude fundamental energy, also included in the transmitted pulse. This example is described in detail in co-pending U.S. Pat. application Ser. No. 09/282,603, filed on the same date as the present specification and hereby incorporated by reference.

2. Any type of transducer, including multi-dimensional transducers—the invention is not limited to piezoelectric transducers or those commonly available on commercial ultrasound systems. For example, the invention may be practiced with electrostatic transducers.

3. Different time-bandwidth products and/or types of amplitude and phase modulation per transmit firing—for example, the time-bandwidth product may be depth dependent when two or more transmit foci are used. To maintain good near field imaging a smaller time-bandwidth product may be preferred for the shallowest focus.

4. The encoding transmitter and decoding receiver can be implemented in different forms. The transmitter and receiver can utilize digital and/or analog circuitry, and the transmit waveform does not necessarily demand a mixer. An example of a suitable transmitter is disclosed in U.S. Pat. No. 5,675,554, "Method and Apparatus for Transmit Beamformer". For example, a simple, digitally-stored waveform can be amplified without a mixer, or an analog oscillator can be swept in time through different frequencies while varying the amplitude. An impulse generator may be used with appropriate complex filters to implement the filters and to generate the desired transmit codes. The receive filtering is not limited to the architectural example given. For example, the demodulation stage need not occur after complete beamformation; instead it can occur on each or a subgroup of receive channels before complete beamformation. Further, receive filtering need not occur at baseband. The complex filtering can be implemented at an intermediate frequency.

5. The invention is not limited to second harmonic signals. Any order integer harmonic or fractional harmonic may be decoded.

6. The invention can be used with simultaneous or temporally sequential acquisition and processing of a coded pulse-compression harmonic B mode image with another type of image, color or B mode, with or without the use of contrast agent. Examples include the following:
    a. Fundamental image with a coded pulse-compression harmonic image.
    b. Fundamental coded pulse-compression image with a coded pulse-compression harmonic image.
    c. Fundamental or harmonic, coded pulse-compression or non-coded color images with a coded pulse-compression harmonic image.

7. The invention can be used with any pre-detected combination of two or more separate beams, spatially collinear or spatially distinct. The individual beams in the combination may have delay profiles with identical amplitudes, frequencies, and phases or may have different amplitudes, frequencies, or phases. An example of this embodiment would include the addition of two beams after pulse-compression receive filtering with opposite polarity transmit phasing to provide improved fundamental signal rejection/cancellation and therefore improved signal bandwidth and axial detail resolution. The associated transmit beams may be spatially aligned as in conventional pulse inversion imaging (e.g. Chapman U.S. Pat. No. 5,632,277) or spatially distinct as described in co-pending U.S. Pat. application Ser. No. 09/282,396, which is hereby incorporated by reference in its entirety.

ALTERNATIVE EMBODIMENTS

The above preferred embodiments describe the application of coded waveforms to tissue harmonic imaging and to imaging with contrast agents. Alternative embodiments are described here specific to contrast agent imaging. One alternative embodiment increases the temporal duration of the transmitted pulses at low pressure amplitudes to improve the SNR without destroying contrast agent. The temporally expanded excitation may be used to excite integer or fractional harmonics of the contrast agents. A second alternative embodiment increases the transmitted pulse durations with pressure amplitudes greater than the pressure amplitudes of the first alternative embodiment, but still less than a maximum, to improve the SNR while some contrast agent may be destroyed. Since optimal image contrast between detected nonlinear contrast agent signals and tissue signals may be obtained at transmit pressures less than the maximum, increased SNR can improve image quality and contrast.

Harmonic imaging of contrast agents increases SNR without loss of resolution when peak amplitudes are maintained and time-bandwidth product and pulse durations are increased as described above. However, there are additional advantages specific to contrast agent imaging such as imaging at low transmit voltages and hence low acoustic pressures. First, using low transmit voltages reduces destruction of the contrast agent. It is believed that a low acoustic pressure transmit pulse with long duration (high time-bandwidth product) will destroy less contrast agent than a compact, high acoustic pressure transmit pulse. Second, at reduced acoustic pressures, contrast agent nonlinear scattering may be increased relative to tissue scattering of the nonlinear propagated harmonic signal. One possible explanation for this is that, at higher acoustic pressures, there is a saturation effect in the scattering from contrast agents, as incident energy is either dissipated or converted to subharmonics or higher order harmonics rather than being converted to second harmonic scattering. The net result is that the contrast between contrast agent harmonic signals and tissue harmonic signals may be greater at low acoustic pressures than at higher acoustic pressures.

For these and possibly other reasons, it may be advantageous to image contrast agents at low acoustic pressures. However, at these lower acoustic pressures, SNR is significantly degraded. Pulse expansion and compression as described generally in this patent may be used to regain some of that SNR without sacrificing axial resolution. In fact, higher time-bandwidth products may be supportable for contrast agent imaging than for tissue harmonic imaging, as the reduction in peak amplitudes allows longer transmit pulses while staying below total pulse energy limits such as FDA limitations on time-averaged pulse power. Time-bandwidth products greater than 100 are impractical for a number of reasons. These long pulses cannot be accurately decoded without producing unacceptably high range lobes when conventional dynamic receive focussing is used, as is common in the industry. To avoid the inaccuracies associated with decoding long pulses with dynamic receive focussing, the pulse-compression filter can be replicated many times and each replica can be placed behind each receive beamforming channel before the dynamic time delays are applied. However, for most practical phased array transducer systems with many elements and system channels, the cost and complexity is prohibitive. Long pulses can also prohibit near field imaging, unless a stand-off pad is used, since conventional receivers cannot listen until the transmitters become inactive.

Nonlinear scattering from contrast agents is considerably more complex than nonlinear propagation through tissues, and models for this scattering may include a number of terms of order x2(t), where x(t) is the incident transmitted pulse. For example, an accurate model may include terms in $$x^2(t),\ x(t)\frac{d^2}{dt^2}x(t),\ \left[\frac{d}{dt}x(t)\right]^2,\ \text{and}\ x(t)\frac{d}{dt}x(t).$$

However, for reasonably smooth phase variations in the transmit pulse and reasonable bandwidths, beneficial results may be obtained using the approximation that the second harmonic scattering from contrast agents is represented by $x^2(t)$. This leads to a scattered second harmonic signal $$Re\{n(t)e^{j4\pi f_m t}\}$$

as in equation 8, where $$n(t)=a^2(t)e^{j2\phi(t)}$$

Of course, somewhat better results may be obtained by using a more accurate model for the nonlinear scattering and designing a receive pulse-compression filter to match the harmonic scattered pulse.

Further beneficial results are obtained by using nonlinear phase modulated transmit pulses with appropriately designed receive pulse-compression filters for imaging contrast agents in combination with alternately phased transmit pulses. Alternating transmit polarity techniques were described above, in particular, item 3 in the Description of FIGS. 2 Through 9 and item 7 of the examples of Preferred Embodiments. In general, reducing the transmit pulse voltage reduces second harmonic signal levels relative to fundamental signal levels from tissue nonlinear propagation, effectively reducing the suppression of the fundamental signals. In addition, using large time-bandwidth products on transmit and receive may result in a reduction in fundamental signal suppression due to finite filter lengths on transmit and receive. In either case, pre-detection combinations of spatially collinear or spatially distinct beams from alternating polarity transmit pulses may be used to increase suppression of the fundamental scattering from tissue. This improves contrast agent specificity and increases axial detail resolution without significant artifacts from unacceptably high fundamental signal levels. The nonlinear phase modulated transmit pulses disclosed above can be modified with an alternating phase term as such $$\phi'(t)=\phi(t)+(n-1)\pi$$

for each consecutively transmitted pulse of index n from 1 to the number of transmitted pulses.

Most of the prior discussion related to both tissue harmonic imaging and contrast agent imaging has concentrated on preferred embodiments in which the receiver performs a matched filtering of the received harmonic pulse. In some cases, it may be desirable to use either a narrower or broader bandwidth on receive than in the transmit pulse. In that case, the receiver is preferably chosen so that the phase distortion (phase vs. frequency) of the receiver compensates for the phase distortion (phase vs. frequency) of the received harmonic pulse. This may include a temporal frequency sweep on receive which differs somewhat from the frequency sweep of the harmonic pulse. For example, if the Gaussian transmit pulse described earlier is used, then the harmonic signal is approximated by $$e^{-2\pi\alpha t^2}e^{j2\pi\gamma t^2}e^{j4\pi f_m t},$$

with duration $T=(2\alpha)^{1/2}$, $$\text{bandwidth } W = \left[\frac{2(\alpha^2+\gamma^2)}{\alpha}\right]^{1/2},$$

and time-bandwidth product given by equation 19. If the receiver is to have a bandwidth $W_R$, then a Gaussian receiver is given by $$e^{-\pi(t/T_R)^2}e^{-j2\pi\gamma_R t^2},$$

where $$T_R = \frac{1}{W_R^2} + \left(\frac{W_R^2}{W^4}\right)[(TW)^2 - 1]$$

and $$\gamma_R = \frac{(\gamma(TW))^2}{(TW)^2 - 1 + \left(\frac{W_R^4}{W^4}\right)}$$

Other arbitrary bandwidth receivers may be designed, but in general, to optimally compress the expanded harmonic signal for best axial resolution, the receiver phase versus frequency is preferably determined to best undo the dispersion (phase vs. frequency) of the incoming harmonic signal. Another way to design pulse-compression receivers, especially when the receiver bandwidth is to be narrower than the harmonic signal bandwidth, is to design an appropriate matched receiver and filter the resulting output signal to reduce the bandwidth. This will ensure optimal compression and therefore axial resolution of the harmonic signal.

It should be noted that ideal transmit and receiver spectra may differ from Gaussian. This is particularly true for integer harmonic or subharmonic imaging, where the transmit and receive spectra are preferably designed to provide maximum axial resolution and signal energy while minimizing the contributions from either the fundamental or from undesired harmonics and subharmonics into the received signal.

One method for designing transmit pulses or pulse compression receive filters of arbitrary spectral shape makes use of the approximation that, for high time-bandwidth products and for monotonic instantaneous frequency modulation, $$|A(f_t)| = \left|A\left(f_m + \left(\frac{1}{2\pi}\right)\frac{d}{dt}[\phi(t)]\right)\right| \approx \frac{k_1|a(t)|}{\left(\left|\left[\frac{d^2}{dt^2}[\phi(t)]\right]\right|\right)^{1/2}},$$

where as described earlier,
A(f) is the pulse spectrum,
$f_t$ is the instantaneous frequency,
$f_m$ is the nominal modulating frequency,
$\phi(t)$ is the phase modulation function, a(t) is the envelope magnitude,
and
$k_1$ is an arbitrary constant. For a quadratic phase modulated pulse with $$\phi(t) = \pi\gamma t^2$$

this reduces to $$|A(f_m + \gamma t)| \approx \frac{k_1 |a(t)|}{(2\pi\gamma)^{1/2}}$$

or $$|A(f_t)| \approx \frac{k_1 \left| a\left(\frac{f_t - f_m}{\gamma}\right) \right|}{(2\pi\gamma)^{1/2}}.$$

This approximation is most valid for high time-bandwidth products, but useful results may be obtained for time-bandwidth products as low as two or four, as may be useful for medical ultrasound applications. The harmonic spectrum associated with the above shaped pulse may be roughly approximated as $$\left| A\left(2f_m + \left(\frac{1}{2\pi}\right)2\frac{d}{dt}([\phi(t)])\right) \right| \approx \frac{k_2 |a(t)|}{\left(\left|\left[\frac{d^2}{dt^2}[\phi(t)]\right]\right|\right)^{1/2}},$$

where $k_2$ is another arbitrary constant.

The foregoing detailed description has discussed only a few of the many forms that this invention can take. For this reason, this detailed description is intended only by way of illustration, and not of limitation. It is only the following claims, including all equivalents, that are intended to define the scope of this invention.

What is claimed is:

1. A medical ultrasound diagnostic imaging method comprising the following steps:
    (a) transmitting a fundamental coded ultrasonic pulse into a tissue, said pulse characterized by a time-bandwidth product less than 100 and greater than 1;
    (b) receiving an Nth harmonic echo signal from the tissue;
    (c) compressing the harmonic echo signal with a compression function having a phase that varies about N times as fast as the fundamental coded ultrasonic pulse.
2. The method of claim 1 wherein N is equal to an integer other than one.
3. The method of claim 1 wherein N is equal to a fraction.
4. The method of claim 1 further comprising the step of
    (d) maintaining the tissue free of added contrast agent during steps (a) and (b).
5. The method of claim 1 further comprising the step of providing a contrast agent in the tissue during steps (a) and (b).
6. The method of claim 1 wherein step (d) comprises the step of maintaining the tissue free of added contrast agent throughout an entire patient examination session during which steps (a), (b) and (c) are performed.
7. The method of claim 1 wherein step (a) comprises the step of launching the pulse from a plurality of transducer elements included in a phased array.
8. The method of claim 1 wherein the pulse is characterized by a time-bandwidth product less than 50.
9. The method of claim 1 wherein the pulse is characterized by a time-bandwidth product less than 20.
10. The method of claim 1 wherein the pulse is characterized by a time-bandwidth product less than 10.
11. The method of claim 1 wherein the pulse is further characterized by an envelope duration and an amplitude modulation function that is symmetric in time about half the envelope duration.
12. The method of claim 1 wherein the pulse is further characterized by an envelope duration and an amplitude modulation function that is asymmetric in time about half the envelope duration.
13. The method of claim 1 wherein the pulse is further characterized by an amplitude modulation function that is substantially uniform.
14. The method of claim 1 wherein the pulse is further characterized by an amplitude modulation function that is continuous in time.
15. The method of claim 1 wherein the pulse is further characterized by an amplitude modulation function that is discontinuous in time.
16. The method of claim 1 wherein the pulse is further characterized by an amplitude modulation function that is substantially non-uniform.
17. The method of claim 1 wherein the pulse is further characterized by a spectral peak and a phase function versus frequency spectrum that is symmetric in frequency about the spectral peak.
18. The method of claim 1 wherein the pulse is further characterized by a spectral peak and a phase function versus frequency spectrum that is asymmetric in frequency about the spectral peak.
19. The method of claim 1 wherein the pulse is further characterized by an envelope duration and a phase function versus frequency spectrum that is symmetric in time about half the envelope duration.
20. The method of claim 1 wherein the pulse is further characterized by an envelope duration and a phase function versus frequency spectrum that is asymmetric in time about half the envelope duration.
21. The method of claim 1 wherein the compression function is further characterized by an envelope duration and an amplitude modulation function that is symmetric in time about half the envelope duration.
22. The method of claim 1 wherein the compression function is further characterized by an envelope duration and an amplitude modulation function that is asymmetric in time about half the envelope duration.
23. The method of claim 1 wherein the compression function is further characterized by an amplitude modulation function that is substantially uniform.
24. The method of claim 1 wherein the compression function is further characterized by an amplitude modulation function that is continuous in time.
25. The method of claim 1 wherein the compression function is further characterized by an amplitude modulation function that is discontinuous in time.
26. The method of claim 1 wherein the compression function is further characterized by an amplitude modulation function that is substantially non-uniform.
27. The method of claim 1 wherein the compression function is further characterized by a spectral peak and a phase function versus frequency spectrum that is symmetric in frequency about the spectral peak.
28. The method of claim 1 wherein the compression function is further characterized by a spectral peak and a phase function versus frequency spectrum that is asymmetric in frequency about the spectral peak.

29. The method of claim 1 wherein the compression function is further characterized by an envelope duration and a phase function versus frequency spectrum that is symmetric in time about half the envelope duration.

30. The method of claim 1 wherein the compression function is further characterized by an envelope duration and a phase function versus frequency spectrum that is asymmetric in time about half the envelope duration.

31. The method of claim 1 wherein the compression function is further characterized by an amplitude modulation function that is continuous in time.

32. The method of claim I wherein the compression function is further characterized by an amplitude modulation function that is discontinuous in time.

33. The method of claim 1 wherein the compression function is further matched in amplitude and phase to the Nth harmonic echo signal at an input of the compression function.

34. The method of claim 1 wherein the compression function is further matched in phase to the Nth harmonic echo signal at an input of the compression function, with an envelope that is different than the transmitted envelope.

35. The method of claim 1 wherein the compression function is further matched in phase to the Nth harmonic echo signal at an input of the compression function, with an envelope that is different than the signal envelope at the input of the compression function.

36. The method of claim 1 wherein the compression function varies as a function of pulse reception time, corresponding to different ranges in tissue.

37. The method of claim 1 wherein multiple pulse compression functions are used simultaneously to decode multiple frequency bands of interest.

38. The method of claim 1 further comprising the steps of
   (d) transmitting a second fundamental coded ultrasonic pulse into the tissue, said second pulse spatially aligned with the pulse of step (a) and differing from the pulse of step (a) in at least one of transmit envelope phase and polarity;
   (e) receiving a second Nth harmonic echo signal from the tissue in response to the second pulse;
   (f) compressing the second harmonic echo signal with a compression function having phase that varies about N times as fast as the second pulse; and
   (g) combining compressed harmonic signals from steps (c) and (f).

39. The method of claim 1 further comprising the steps of
   (d) transmitting at least two additional fundamental coded ultrasonic pulses into the tissue, said additional pulses spatially aligned with the pulse of step (a) and differing from the pulse of step (a) in at least one of transmit envelope phase and polarity;
   (e) receiving additional Nth harmonic echo signals from the tissue in response to the additional pulses of step (d);
   (f) compressing the additional Nth harmonic echo signals with a compression function having a phase that varies about N times as fast as the additional pulses; and
   (g) combining compressed harmonic signals from steps (c) and (f).

40. The method of claim 1 further comprising the steps of
   (d) transmitting a second fundamental coded ultrasonic pulse into the tissue, said second pulse spatially distinct from the pulse of step (a) and differing from the pulse of step (a) in at least one of transmit envelope phase, and polarity;
   (e) receiving a second Nth harmonic echo signal from the tissue in response to the second pulse;
   (f) compressing the second harmonic echo signal with a compression function having phase that varies about N times as fast as the second pulse; and
   (g) combining compressed harmonic signals from steps (c) and (f).

41. The method of claim 1 further comprising the steps of
   (d) transmitting at least two additional fundamental coded ultrasonic pulses into the tissue, said additional pulses spatially distinct from the pulse of step (a) and differing from the pulse of step (a) in at least one of transmit envelope phase and polarity;
   (e) receiving additional Nth harmonic echo signals from the tissue in response to the additional pulses of step (d);
   (f) compressing the additional Nth harmonic echo signals with a compression function having a phase that varies about N times as fast as the additional pulses; and
   (g) combining compressed harmonic signals from steps (c) and (f).

42. A medical ultrasound diagnostic imaging system comprising:
   a phased array transducer probe;
   a transmitter coupled with the mode and operative to supply transmit waveforms thereto, said transmit waveforms causing the probe to transmit a fundamental coded ultrasonic pulse into a tissue characterized by a time-bandwidth product less than 100 and greater than 1;
   a receiver coupled with the probe and operative to receive an Nth harmonic echo signal from the tissue; and
   a compression filter operative to compress the harmonic echo signal with a compression function having a phase that varies about N times as fast as the fundamental coded ultrasonic pulse.

43. The invention of claim 42 wherein N is an integer other than one.

44. The method of claim 42 wherein N is equal to a fraction.

45. The method of claim 42 wherein the pulse is characterized by a time-bandwidth product less than 50.

46. The invention of claim 42 wherein the time-bandwidth product is less than 20.

47. The invention of claim 42 wherein the time-bandwidth product is less than 10.

48. The invention of claim 42 wherein the pulse is further characterized by an envelope duration and an amplitude modulation function that is symmetric in time about half the envelope duration.

49. The invention of claim 42 wherein the pulse is further characterized by an envelope duration and an amplitude modulation function that is asymmetric in time about half the envelope duration.

50. The method of claim 42 wherein the pulse is further characterized by an amplitude modulation function that is substantially uniform.

51. The method of claim 42 wherein the pulse is further characterized by an amplitude modulation function that is continuous in time.

52. The method of claim 42 wherein the pulse is further characterized by an amplitude modulation function that is discontinuous in time.

53. The method of claim 42 wherein the pulse is further characterized by an amplitude modulation function that is substantially non-uniform.

54. The invention of claim 42 wherein the pulse is further characterized by a spectral peak and a phase function versus frequency spectrum that is symmetric in frequency about the spectral peak.

55. The invention of claim 42 wherein the pulse is further characterized by a spectral peak and a phase function versus frequency spectrum that is asymmetric in frequency about the spectral peak.

56. The method of claim 42 wherein the pulse is further characterized by an envelope duration and a phase function versus frequency spectrum that is symmetric in time about half the envelope duration.

57. The method of claim 42 wherein the pulse is further characterized by an envelope duration and a phase function versus frequency spectrum that is asymmetric in time about half the envelope duration.

58. The method of claim 42 wherein the compression function is further characterized by an envelope duration and an amplitude modulation function that is symmetric in time about half the envelope duration.

59. The method of claim 42 wherein the compression function is further characterized by an envelope duration and an amplitude modulation function that is asymmetric in time about half the envelope duration.

60. The method of claim 42 wherein the compression function is further characterized by an amplitude modulation function that is substantially uniform.

61. The method of claim 42 wherein the compression function is further characterized by an amplitude modulation function that is substantially non-uniform.

62. The method of claim 42 wherein the compression function is further characterized by a spectral peak and a phase function versus frequency spectrum that is symmetric in frequency about the spectral peak.

63. The method of claim 42 wherein the compression function is further characterized by a spectral peak and a phase function versus frequency spectrum that is asymmetric in frequency about the spectral peak.

64. The method of claim 42 wherein the compression function is further characterized by an envelope duration and a phase function versus frequency spectrum that is symmetric in time about half the envelope duration.

65. The method of claim 42 wherein the compression function is further characterized by an envelope duration and a phase function versus frequency spectrum that is asymmetric in time about half the envelope duration.

66. The method of claim 42 wherein the compression function is further characterized by an amplitude modulation function that is continuous in time.

67. The method of claim 42 wherein the compression function is further characterized by an amplitude modulation function that is discontinuous in time.

68. The method of claim 42 wherein the compression function is further matched in amplitude and phase to the Nth harmonic echo signal at an input of the compression function.

69. The method of claim 42 wherein the compression function is further matched in phase to the Nth harmonic echo signal at an input of the compression function with an envelope that is different than the transmitted envelope.

70. The method of claim 42 wherein the compression function is further matched in phase to the Nth harmonic echo signal at an input of the compression function, with an envelope that is different than the signal envelope at the input of the compression function.

71. The method of claim 42 wherein the compression function varies as a function of pulse reception time, corresponding to different ranges in tissue.

72. The method of claim 42 wherein multiple pulse compression functions are used simultaneously to decode multiple frequency bands of interest.

* * * * *

UNITED STATES PATENT AND TRADEMARK OFFICE
CERTIFICATE OF CORRECTION

PATENT NO.   : 6,241,674 B1
DATED        : June 5, 2001
INVENTOR(S)  : Patrick Phillips et al.

It is certified that error appears in the above-identified patent and that said Letters Patent is hereby corrected as shown below:

Column 4,
Line 37, delete "$X^1$" and substitute -- $X'$ -- in its place.

Column 7,
Equation 20, delete "$X^1_{tX}{}^1 = \text{Re}\{e^{-\pi\alpha r^2} e^{j\pi\gamma r^2} e^{j2\pi f_m t}\},$" and substitute -- $X'_{tx} = \text{Re}\{e^{-\pi\alpha t^2} e^{j\pi\gamma t^2} e^{j2\pi f_m t}\},$ -- in its place.

Equation 23, delete "$X_{rx}(t) = j D_3 e^{-2\pi\alpha t^2} e^{-j2\pi\gamma t^2},$" and substitute -- $X_{rx}(t) = j D_3 e^{-2\pi\alpha t^2} e^{-j2\pi\gamma t^2},$ -- in its place.

Column 11,
In all four equations, delete "$^f m$" and substitute -- $f_m$ -- in its place, in all occurrences.

Column 12,
Line 11, delete "i.e," and substitute -- i.e., -- in its place.

Column 16,
Line 8, delete "$e^{-2\pi\alpha r^2} e^{j2\pi\gamma r^2} e^{j4\pi f_m t}$" and substitute -- $e^{-2\pi\alpha t^2} e^{j2\pi\gamma t^2} e^{j4\pi f_m t}$ -- in its place.

Line 20, delete "$e^{-\pi(t/T_R)^2} e^{-j2\pi\gamma_R r^2}$" and substitute

-- $e^{-\pi(t/T_R)^2} e^{-j2\pi\gamma_R t^2}$ -- in its place.

UNITED STATES PATENT AND TRADEMARK OFFICE
CERTIFICATE OF CORRECTION

PATENT NO.   : 6,241,674 B1
DATED        : June 5, 2001
INVENTOR(S)  : Patrick Phillips et al.

It is certified that error appears in the above-identified patent and that said Letters Patent is hereby corrected as shown below:

Column 17,
Line 6, delete " $\phi(t) = \pi \gamma r^2$ " and substitute -- $\phi(t) = \pi \gamma t^2$ -- in its place.

Signed and Sealed this

Thirty-first Day of December, 2002

JAMES E. ROGAN
*Director of the United States Patent and Trademark Office*